(12) United States Patent
Doguet et al.

(10) Patent No.: US 11,944,832 B2
(45) Date of Patent: Apr. 2, 2024

(54) ACTIVE IMPLANTED DEVICE (AIMD) WITH IN SITU OPTIMIZATION OF POWER CONSUMPTION

(71) Applicant: Synergia Medical, Mont-Saint-Guibert (BE)

(72) Inventors: Pascal Doguet, Mont-Saint-Guibert (BE); Jérôme Garnier, Mont-Saint-Guibert (BE); Yohan Botquin, Mont-Saint-Guibert (BE)

(73) Assignee: Synergia Medical, Mont-Saint-Guibert (BE)

( * ) Notice: Subject to any disclaimer, the term of this patent is extended or adjusted under 35 U.S.C. 154(b) by 0 days.

(21) Appl. No.: 18/371,044

(22) Filed: Sep. 21, 2023

(65) Prior Publication Data

US 2024/0009470 A1    Jan. 11, 2024

Related U.S. Application Data

(63) Continuation-in-part of application No. PCT/EP2021/057548, filed on Mar. 24, 2021.

(51) Int. Cl.
*A61N 1/37* (2006.01)
*A61N 1/378* (2006.01)
*H02S 99/00* (2014.01)

(52) U.S. Cl.
CPC .............. *A61N 1/378* (2013.01); *H02S 99/00* (2013.01)

(58) Field of Classification Search
CPC ...................................................... A61N 1/378
See application file for complete search history.

(56) References Cited

U.S. PATENT DOCUMENTS

| | | | |
|---|---|---|---|
| 2010/0048982 A1* | 2/2010 | Puria | H04R 23/008 607/57 |
| 2017/0368358 A1* | 12/2017 | Doguet | A61N 1/3787 |
| 2020/0206514 A1* | 7/2020 | Doguet | A61N 1/378 |
| 2022/0143418 A1* | 5/2022 | Cortese | A61B 1/0605 |

FOREIGN PATENT DOCUMENTS

| | | |
|---|---|---|
| EP | 3113838 B1 | 6/2017 |
| EP | 3471820 A1 | 4/2019 |
| EP | 3687623 A1 | 8/2020 |
| WO | 2021008688 A1 | 1/2021 |

OTHER PUBLICATIONS

Int'l Search Report for PCT/US2021/057548, dated Jan. 4, 2022.

* cited by examiner

*Primary Examiner* — Eric D. Bertram
(74) *Attorney, Agent, or Firm* — MaxGoLaw PLLC

(57) ABSTRACT

An active implantable medical device (AIMD), for electrical stimulation of a tissue includes a light source, lodged in an encapsulation unit, for delivering optical energy pulses of optical power (Popt). A stimulation optical fibre for transferring optical energy from the light source of the encapsulation unit to the tissue coupling unit is also provided. The tissue coupling unit is configured for being coupled to a tissue to be electrically stimulated by electrodes (65) belonging to an electrical circuit. The PV-unit includes Us units arranged in series, each unit having Pp photovoltaic cells (PV-cells) arranged in parallel. Us and Pp, $\in N$, and Us×Pp=N=constant. The electrical circuit includes switches configured for varying the values of Us and alternatively or concomitantly, the light source is an addressable optical emitters array.

18 Claims, 7 Drawing Sheets

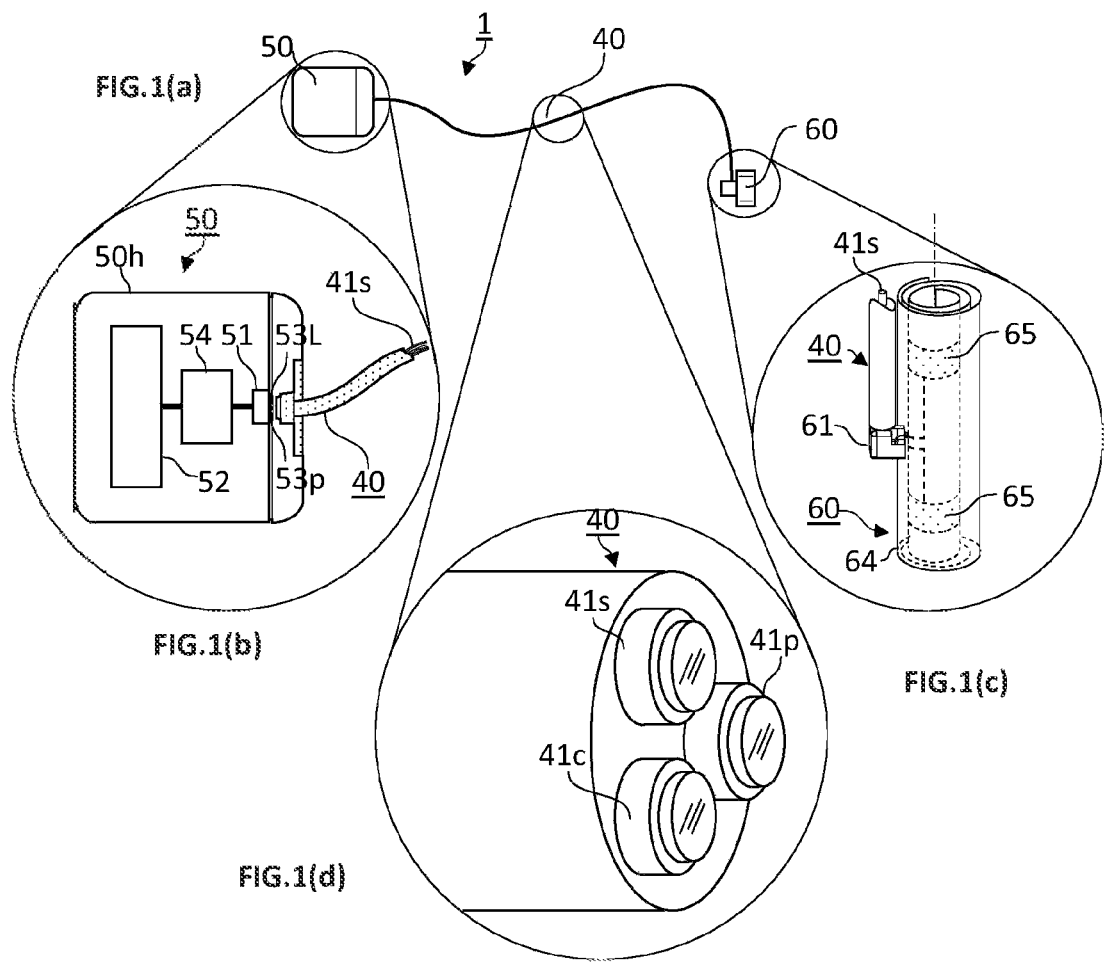
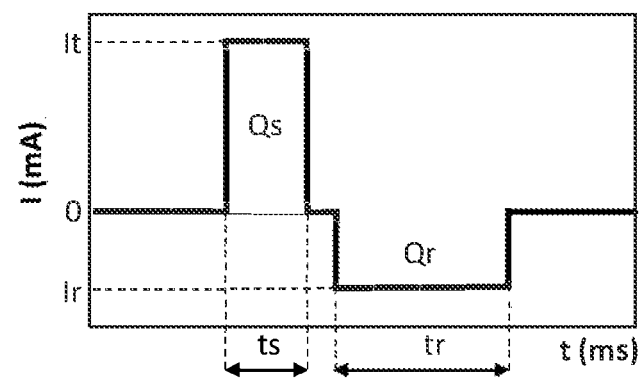

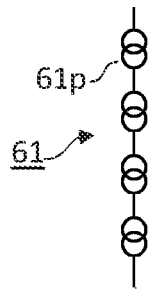
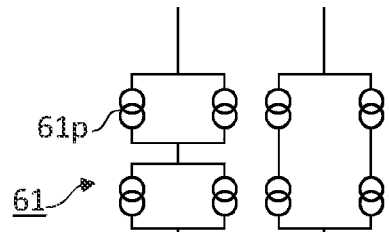
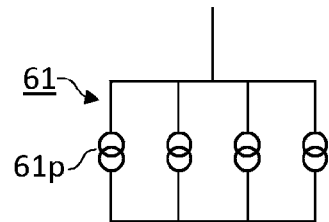
FIG.2(a)  FIG.2(b)  FIG.2(c)
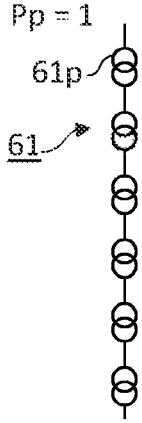
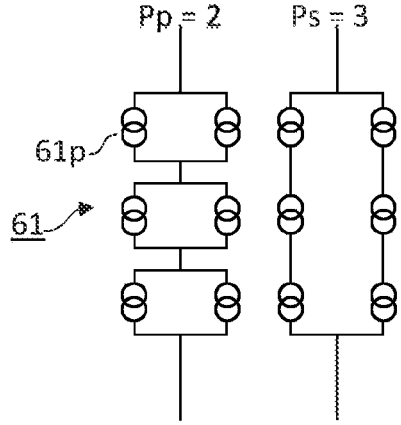
FIG.3(a)  FIG.3(b)
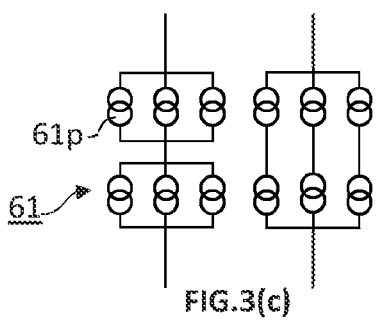
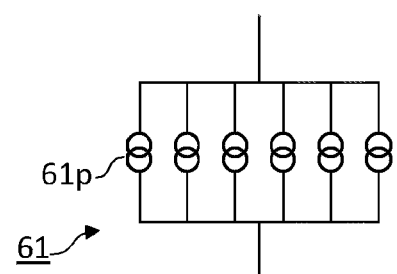
FIG.3(c)  FIG.3(d)

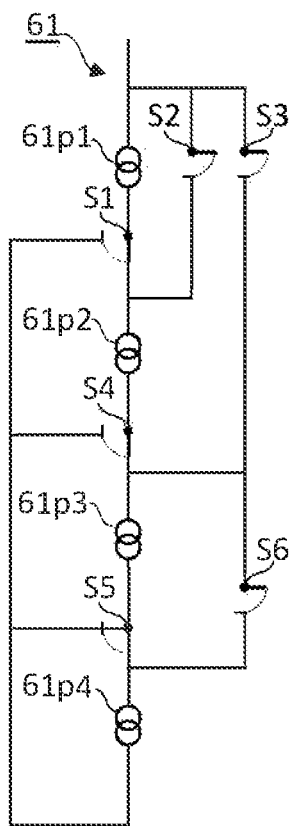
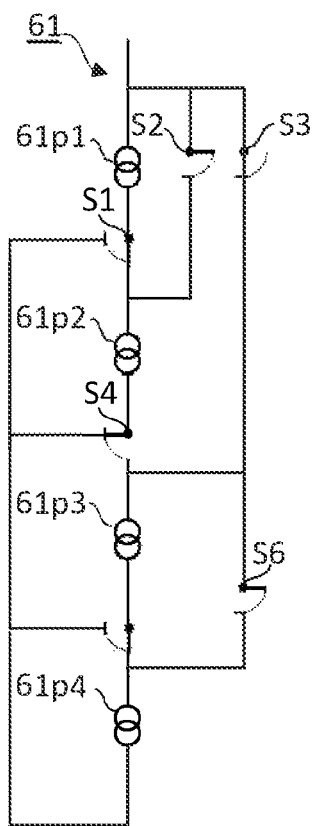
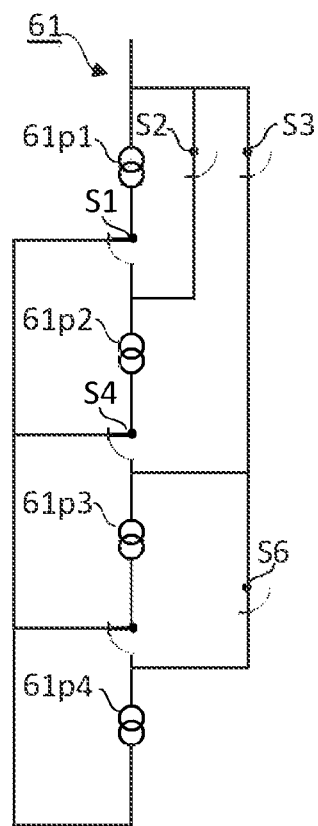
N = 4    N = 4
Us = 4   Up = 1
Pp = 1   Ps = 4
N = 4    N = 4
Us = 2   Up = 2
Pp = 2   Ps = 2
N = 4    N = 4
Us = 1   Up = 4
Pp = 4   Ps = 1
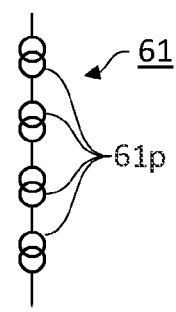
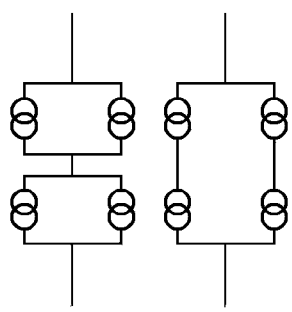
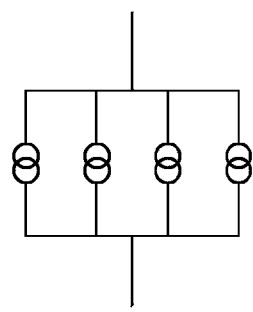
FIG.4(a)　　　　　FIG.4(b)　　　　　FIG.4(c)

ACTIVE IMPLANTED DEVICE (AIMD) WITH IN SITU OPTIMIZATION OF POWER CONSUMPTION

RELATED APPLICATIONS

This application is a continuation-in-part of International Application No. PCT/EP2021/057548, filed 24 Mar. 2021, which in turn claims priority benefit EP4114514, filed 24 Mar. 2021, the contents of the aforementioned priority documents are hereby incorporated by reference.

TECHNICAL FIELD

The present invention concerns an active implantable medical device (AIMD) configured for being implanted in a body of a patient. The AIMD of the present invention is an opto-neurostimulator (=opto-AIMD) comprising one or more energy transfer chains for transferring energy pulses from an IPG to electrodes. Each energy transfer chain comprises a light source for emitting optical pulses, an optical fibre for transferring the optical pulses, and a photovoltaic (PV-) unit for transforming the optical pulses into electrical pulses for creating a current of target intensity (It) between the electrodes. The opto-AIMD of the present invention allows fine-tune in situ optimization of the energy transfer chain after implantation of the opto-AIMD into a patient's body depending on the measured impedance (Z) between the electrodes, to reduce battery power (Pbat) consumption. In particular, the opto-AIMD of the present invention allows optimization of, on the one hand, the photovoltaic cells configuration constituting the PV-unit and, on the other hand, the configuration of the light source. In situ optimization of any one of or of both PV-unit and light source yields substantial reduction of battery power consumption.

BACKGROUND OF THE INVENTION

Active implantable medical devices (AIMD) have been used for decades for treating a number of disorders, in particular neurological disorders. Active implantable medical devices (AIMD) distinguish from (non-active) implantable medical devices (IMD), like RFID tags and the like, in that AIMD's are configured for actively interacting with the body they are implanted in, such as by stimulating tissues, monitoring vital signs, and the like. Generally, AIMD's are able to transfer energy from and to the implant. AIMD's therefore generally enclose a source of power, such as a battery, preferably a rechargeable battery.

A major type of AIMD's consists of neurostimulators, which deliver electrical pulses to a neural tissue (e.g., such as a nerve like the vagus nerve or brain tissue) or a muscle for diagnosing or treating a number of disorders such as Parkinson's disease, epilepsy, chronic pain, motor disorders, and many other applications. Depending on the tissue to be treated, the type of electrodes used, and the distance between electrodes, the voltage required between implanted electrodes is generally of the order of 1 to 10 V. Such voltage requires an electrical pulse generator and a battery of such dimensions that electric stimulating implants are generally formed of two separate components as illustrated in FIG. 1(a). On the one hand, the electrodes which are implanted directly onto the tissue to be treated and, on the other hand, the electrical pulse generator, of larger dimensions, and enclosed in an encapsulation unit, which can be implanted subcutaneously at various locations in the body depending upon the application. The encapsulation can be implanted in the cranial region, the subclavian region, the lower abdominal area or gluteal region, and the like. The encapsulation unit is generally made of titanium (alloys) for its mechanical properties and for other reasons, such as biocompatibility and easy processability. Encapsulations made of titanium have, however, low to no transmission to RF, visible and IR wavelengths, and are not MRI-friendly, generating heat and imaging artefacts. Some encapsulations have been made in ceramic materials, opaque or transparent to visible and IR lights. Polymers have been tested for encapsulations, but they generally lack durability and resistance to moisture.

As shown in FIG. 1(a), in its simplest form, a device for delivering energy pulses comprises an implantable pulse generator (IPG) lodged in a housing of an encapsulation unit, a tissue coupling unit, and an energy transfer lead coupling the tissue coupling unit to the IPG to transmit energy from the IPG to the tissue coupling unit in the form of electrical or optical energy. An optically powered AIMD (=opto-AIMD) such as an opto-neurostimulator is a specific type of AIMD generating and transmitting optical pulses through an optical fibre to a photovoltaic cell, transforming the optical energy into electrical energy to apply a voltage difference between the electrodes of the tissue coupling unit is described, e.g., in EP3113838B1. Opto-AIMD are advantageous inter alia in that they show substantially higher MRI compatibility than 'conventional' neurostimulators generating electrical pulses which are conducted to the electrodes through conductive wires. Opto-neurostimulators, however, have a number of challenges to be addressed.

In particular, when in 'conventional' neurostimulators electrical pulses generated by the IPG are transmitted directly to the electrodes through conductive wires, in opto-neurostimulators electrical pulses are transmitted via an energy transfer chain comprising, a light source belonging to the IPG and lodged in the encapsulation unit for generating optical energy pulses,
an optical feedthrough in the form of a window to transfer the optical energy pulses to,
an optical fibre optically connecting the light source of the encapsulation unit to the tissue coupling unit to,
a photovoltaic (PV-) unit belonging to the tissue coupling unit for transforming the optical energy pulses into electrical pulses of target intensity (It), and
short conductive wires leading to the electrodes.

To ascertain that an emitted optical pulse did activate the vagus nerve, EP3687623 describes an optical AIMD comprising an external controller device configured for detecting an electrical signal at the level of a laryngeal region indicative that the vagus nerve was actually activated following the emission of an optical pulse.

Communication between an implanted AIMD and an exterior of the body can also be carried out optically, as described e.g., in WO2021008688. Such optical communication also consumes power from the battery. It is therefore important to optimize the various optical energy transfers emitted by the AIMD. For example, EP3471820 describes a coupling module between one or more optical fibres and the tissue coupling unit provided with one or more photovoltaic cells, allowing an excellent alignment between the one or more optical fibres and the corresponding one or more photovoltaic cells.

Unlike the direct transmission of electrical pulses in 'conventional' neurostimulators, the energy transfer chain of opto-neurostimulators (=opto-AIMD) generates energy losses at various stages, which can be substantial if not carefully optimized. A light pulse generated by a light source of the IPG is transmitted out of the encapsulation unit through a window (sometimes referred to as an optical feedthrough) and to the tissue coupling unit via an optical fibre. Both window and optical fibre absorb or reflect part of the optical energy, which must be taken into account for transmitting an optical pulse of required optical power (Popt) for generating an electrical current of target intensity (It) at the electrodes. The optical pulse of power (Popt) irradiates an array of photovoltaic cells (PV-cells) which transforms the optical energy into an electrical current of given intensity and a corresponding voltage. The energy transformation process is limited inter alia by the number and performance of the photovoltaic cells and by their configuration in the array. The conversion of an optical pulse of given power (Popt) by a PV-cell or by a given array of PV-cells into electrical current between the electrodes is governed by an I=f(U) (or (I-u)) characteristic curve of the type illustrated in FIG. 7. The (I-u)-output of a (array of) PV-cell is characterized by the PV-cell (I-u) characteristic curve, I=f(u), an example of which is illustrated in FIG. 7, solid line. By connecting the PV-cell (array) to an impedance (Z) downstream thereof, a current (I) and voltage (u) are generated which values are defined by the intersection of the impedance curve (1/Z) (cf. FIG. 7, long, dashed line) with the (I-u) characteristic curve. The (P-u) curve (cf. FIG. 7, short, dashed line) is indicative of how efficiently the PV-cell or PV-cells array is used. The maximum of the (P-u) curve is called the maximum power point or point of maximum efficiency (MPP), corresponding to a power of maximum efficiency (Pe) reached at a maximum efficiency voltage (ue). It is obviously desirable to use the PV-cell or given array of PV-cells as close as possible to the point of maximum efficiency (MPP). This is traditionally achieved by tracking the maximum power point (=MPPT for "maximum power point tracking") for generating a given target intensity (It) by varying the value of the impedance (Z) downstream of the PV-cell such as to intersect the (I-u) curve at the corresponding target voltage (ut) equal to (or at least lower than and as close as possible to) the value of the maximum efficiency voltage (ut≲ue). MPPT is extensively used to optimize the efficiency of e.g., solar panels. With opto-AIMD's, however, it is not possible to control, let alone vary, the value of the impedance downstream of the PV-cell or given PV-cells array. Indeed, the impedance (Z) depends inter alia on the one hand, on the nature and conditions of the tissue, which of course varies from patient to patient and, on the other hand, on the electrical contact between the electrodes and the tissue they are coupled to, which can depend on the conditions encountered by the surgeon implanting the tissue coupling unit to a tissue or on movements of the patient. There is no way to predict the value of impedance prior to implanting and testing the opto-AIMD. For these reasons, MPPT as discussed supra cannot be used to optimize the efficiency of use of PV-cells in opto-AIMD's. In the present documents, ideal (I-u) characteristic curves are presented for sake of clarity, with the intensity remaining constant until saturation. In practice, the portion where I(u) is represented as constant may deviate a little from horizontal and slope downwards a little because of shunt resistance for example. This slight dependence of I as a function of u does not affect the present discussion and can easily be accounted for by a person skilled in the art.

Absent a way of controlling the impedance (Z) downstream of the PV-cells, a PV-unit can be optimized during production in factory only up to a certain point, as the value of the impedance (Z) and thus of the target voltage (ut) are missing and can only be estimated within a rather broad range. Opto-AIMD's producers must therefore "oversize" the characteristics of the PV-cells to ensure that a first patient requiring pulses of target intensity (It) prescribed by a medical practitioner and presenting a high value of impedance (Z) can be treated with a same opto-AIMD as a second patient requiring pulses of the same intensity (It) and presenting lower values of impedance (Z). The opto-AIMD will therefore work sub-optimally (i.e., remote from the point of maximum efficiency (MPP)) with at least the second patient.

Like for the PV-unit, optimization of the source of light can be achieved during production in factory up to a certain point only, for the following reasons. First, the target intensity (It) of the current to be delivered to a tissue is determined by a medical practitioner on a case-by-case basis and depends on the pathology and patient to be treated. Second, the efficiency with which the optical power (Popt) is used for generating a current of target intensity (It) to be delivered to the tissue depends inter alia on the impedance (Z) of the portion of tissue comprised between the electrodes relative to the point of maximum efficiency (MPP) the PV-cell or PV-cells array forming the PV-unit. The target intensity (It) can only be known once the opto-AIMD has been assigned to a specific patient, and the impedance (Z) can only become known after the opto-AIMD has been implanted and tested in situ in the patient.

For these reasons again, opto-neurostimulators are generally designed for a worst-case scenario, allowing dispensing currents of relatively high intensities, assuming a relatively high value of the impedance (Z) between the electrodes. In practice, however, in most applications, the values of the target intensity required by the medical practitioner and the values of the impedance measured between the electrodes are substantially lower than the ones the opto-neurostimulators has been designed for. In other words, if an opto-neurostimulator was designed for delivering electrical pulses of estimated intensity (I0), for an estimated impedance (Z0), such that an estimated voltage (u0=Z0×I0) is close to or equal to the maximum efficiency voltage (ue) (i.e., ue−u0≃0), it is clear that this opto-neurostimulator would be suboptimized for use in a patient with a measured impedance (Z<Z0), to be treated with electrical pulses of target intensity (It<I0), as the value of the target voltage would thus shift away from the value of the maximum efficiency voltage (i.e., |ue−ut|>0≃|ue−u0|). The power difference, It×|ue−ut|, represents power wasted and dissipated in heat and the like, relative to an optimal use of the PV-cells. If ut=ue, then the optical power furnished to the PV-cells is used optimally.

For example, an opto-AIMD may be designed to generate pulses of estimated intensities of the order of I0=3 mA and an estimated impedance (Z0) of the order of 1.5 kΩ, yielding a corresponding estimated voltage, u0=1.5 kΩ×3 mA=4.5 V. In the vast majority of cases, however, target intensities (It) of the order 1 mA may be prescribed by the medical practitioner and impedances (Z) of the order of 1 kit (generally ranging from 0.3 to 1.5 kΩ) may be measured in many patients, yielding values of the target voltage (ut=Z×It) of the order of 1 V only (i.e. ut=1 V<u0=4.5 V). An opto-AIMD designed for generating pulses of target intensities of It=3 mA with impedances of 1.5 kΩ should be provided with a PV-unit having a value of the maximum efficiency voltage (ue) of the order of 4.5 V (i.e., ue≃4.5 V). Such opto-AIMD is suitable for delivering pulses of target intensity of It=1 mA with impedances of 1 kΩ, but the opto-AIMD would thus function in suboptimal conditions in terms of efficiency since the target voltage (ut=1 V) would be far remote from the maximum efficiency voltage (ue≃4.5 V). It follows that a substantial portion of the optical power (Popt) delivered to the PV-cells is not used for generating a current of target intensity (It), and is dissipated instead in heat and the like. This has the major drawback for implanted opto-AIMD's, that a higher battery power (Pbat) is required to deliver the target intensity (It) to the electrodes than would be required should the opto-AIMD function in optimal conditions in terms of efficiency. Saving battery power is a major objective in opto-AIMD's, as it prolongs the service life of an implanted opto-AIMD and, in case of rechargeable batteries, it increases the time between two charging sessions, which are quite cumbersome and uncomfortable for the patient.

As illustrated in FIG. 1(e), it is preferred, upon sending to the electrodes a stimulation pulse or a train of stimulation pulses of electrical current of target intensity (It) during a stimulation time (ts), to sequentially follow it by sending a recovery pulse of recovery intensity (Ir) during a recovery time (tr), in order to prevent accumulation of charges in the tissues of the patient. The recovery pulses are such that, a ratio, Ir/It<0, i.e., the recovery intensity has a sign opposite to the target intensity,

|It|≥|Ir|, and

|Qs|=|It×ts|≃|Qr|=|Ir×tr|, wherein Qs and Qr are the stimulation and recovery charges deposited on the tissue, respectively.

To avoid duplication of the energy transfer chains between the encapsulation unit and the tissue coupling unit, for sending stimulation and recovery pulses, it is preferred to use the same energy transfer chain for transferring both stimulation pulses and recovery pulses, i.e., using the same light source, the same optical fibre, and the same PV-unit. Since |It|>|Ir|, however, an energy transfer chain of an opto-neurostimulator pre-designed for worst case scenarios (i.e., high values of estimated intensity (I0) and of estimated impedance (Z0)) which functions sub-optimally for stimulation pulses of target intensity (It) smaller than the estimated intensity (I0) (cf. discussion supra) is even less optimal for transferring recovery pulses of recovery intensity (Ir) of lower magnitude than the target intensity (It) (i.e., Ir<It<I0). This is detrimental to the battery power (Pbat) consumption and, ultimately, to the comfort of the patient.

The present invention proposes a solution for reducing the energy consumption of an implanted opto-AIMD depending on the tissue impedance measured directly on the patient. For the first time to our knowledge, with the opto-AIMD of the present invention, optimization of the energy transfer chain can be completed in situ after the opto-AIMD has been implanted in the patient. These and other advantages of the present invention are presented in continuation.

SUMMARY OF THE INVENTION

The present invention is defined in the appended independent claims. Preferred embodiments are defined in the dependent claims. In particular, the present invention concerns an active implantable medical device (AIMD), for electrical stimulation of a tissue, the AIMD comprising:

an encapsulation unit suitable for being subcutaneously implanted and comprising a housing enclosing,
   an implanted energy pulse generator (IPG) coupled to a light source, for delivering optical energy pulses of optical power (Popt),
   a source of power for activating the IPG and configured for generating a battery power (Pbat) which can be varied,
   an implanted controller configured for instructing the IPG to deliver optical energy pulses of a given optical power (Popt) as a function of time, and
an implanted energy transfer unit comprising a stimulation optical fibre comprising a proximal end optically coupled to the light source, and a distal end coupled to a tissue coupling unit, for transferring optical energy from the light source of the encapsulation unit to the tissue coupling unit,
the tissue coupling unit suitable for being subcutaneously implanted and coupled to a tissue at a location separated from the encapsulation unit, and comprising,
   an insulating support supporting,
   an electrical circuit configured for delivering electrical pulses of a given target intensity (It) and comprising,
      a photovoltaic unit (PV-unit) comprising N≥2 photovoltaic (PV) cells, positioned in optical contact with the distal end of the optical fibre for transforming the optical energy pulses transmitted by the optical fibre into electrical energy pulses of the target intensity (It),
      electrical conductors for transferring the electrical energy pulses to
      electrodes mounted on the insulation support such as to be in electrical contact with the tissue when the insulation support is coupled to the tissue.

The gist of the invention is that,

The PV-unit comprises Us units arranged in series, each unit comprising Pp photovoltaic cells (PV-cells) arranged in parallel, or Up units arranged in parallel, each unit comprising Ps PV-cells arranged in series, wherein Us, Up, Pp, and Ps∈N, and Us×Pp=Up×Ps=N=constant, the electrical circuit comprises switches configured for varying the values of Us and Up, and that the electrical circuit comprises a switch control module configured for controlling the switches yielding optimized values of Us or Up, such that the power (Popt) of the optical energy pulses required for yielding the electrical pulses of the given target intensity (It) is minimized.

In a preferred embodiment, the AIMD comprises a regulation unit configured for determining the optimized values of Us or Up, wherein the electrical circuit comprises a sensing unit configured for measuring values of a voltage (u) and/or an intensity (I) of the electrical pulses delivered to the electrodes, and wherein measured values of the voltage (u) and/or intensity (I) are used by the regulation unit for optimizing the values of Us or Up. The regulation unit can for example be configured for determining the optimized values of Us or Up, as follows, for a given value of the optical power (Popt), determining or measuring a target voltage (ut) corresponding to the target intensity (It) when the AIMD is implanted with the tissue coupling unit coupled to a tissue, determining an optimal value of Us or Up yielding a maximum voltage (um1, um2, um4) which is larger than, and the closest to the value of the target voltage (ut), adjusting the power (Popt) of the optical energy pulses to an optimal optical power (Popt1, Popt2, Popt4) required to reach the target intensity (It) with the optimal value of Us or Up.

For example, the regulation unit can be configured for determining or measuring the target voltage (ut) as follows, either generating and transmitting optical pulses of a given optical power (Popt) known to yield upon irradiation of the PV-unit with Us=N, a current of the target intensity (It), and measuring a voltage between the electrodes (61) which corresponds to the target voltage (ut), or for any given value of the optical power (Popt) and with Us=N,
- measuring a voltage (u) and an intensity (I) between the electrodes (61),
- determining an impedance (Z) with $|Z|=|u|/|I|$ and
- calculating the target voltage (ut) with $|ut|=|Z|\times|It|$.

The light source is preferably an addressable optical emitters array, preferably an array of addressable laser emitter diodes, more preferably of vertical cavity surface-emitting laser (VCSEL), or an array of addressable light emitting diodes (LED), the optical emitters array comprising M>1 apertures addressable independently one by one or by sub-groups of apertures. Once the regulation unit has determined the optimal value of Us requiring an optimal optical power value (Popt=Popt1, Popt2, or Popt4) for generating the target intensity (It), the regulation unit is configured for then determining an optimal number (m≤M) of apertures addressed at a time such as to minimize the battery power (Pbat) required to generate the optimal optical power (Popt=Popt1, Popt2, or Popt4)

The present invention also concerns an AIMD for electrical or optical stimulation of a tissue, the AIMD comprising:
- an encapsulation unit suitable for being subcutaneously implanted and comprising a housing enclosing,
  - an implanted energy pulse generator (IPG) coupled to a light source, for delivering optical energy pulses of optical power (Popt),
  - a source of power for activating the IPG and configured for generating a battery power (Pbat) which can be varied,
  - an implanted controller configured for instructing the IPG to deliver optical energy pulses of a given power (Popt) as a function of time, and
- an implanted energy transfer unit comprising a stimulation optical fibre comprising a proximal end optically coupled to the light source, and a distal end coupled to a tissue coupling unit, for transferring optical energy from the light source of the encapsulation unit to the tissue coupling unit,
- the tissue coupling unit is suitable for being subcutaneously implanted and coupled to a tissue at a location separated from the encapsulation unit and comprises,
  - an insulating support supporting,
    - either an optrode, or an electrical circuit configured for delivering electrical pulses of a given target intensity (It) and comprising,
      - a photovoltaic unit (PV-unit) comprising one or more photovoltaic (PV) cells, positioned in optical contact with the distal end of the optical fibre for transforming the optical energy pulses transmitted by the optical fibre into electrical energy pulses of the target intensity (It),
      - electrical conductors for transferring the electrical energy pulses to
      - electrodes mounted on the insulation support such as to be in electrical contact with the tissue when the insulation support is coupled to the tissue.

The AIMD is characterized in that,
the light source is an addressable optical emitters array, preferably an array of addressable laser emitter diodes, more preferably of vertical cavity surface-emitting laser (VCSEL), or an array of addressable light emitting diodes (LED), the optical emitters array comprising M>1 apertures addressable independently one by one or by sub-groups of apertures, an in that the implanted controller is configured for determining an optimal number (m≤M) of apertures addressed at a time such as to minimize the battery power (Pbat) to generate the optimal optical power (Popt).

The AIMD can comprise a comprising a regulation unit as defined supra, which either,
- is fully integrated in the implanted controller and is configured for determining,
  - the values of the voltage (u) and/or the intensity (I) of the electrical pulses delivered to the electrodes measured by the sensing unit,
  - the optimal values of Us and Pp for reaching the target intensity (It), in an AIMD as described supra,
  - the optimal optical power (Popt) as described supra,
- comprises a coupling portion belonging to the electrical circuit of the tissue coupling unit (60) and is configured for determining,
  - the values of the voltage (u) and/or the intensity (I) of the electrical pulses delivered to the electrodes measured by the sensing unit,
  - the optimal value of Us or Up and the optimal optical power (Popt) of the optical energy pulse for reaching the target intensity (It), in an AIMD according to claim 3 or 4, and
- comprises an encapsulated portion belonging to the implanted controller in the encapsulation unit and is configured for determining,
  - the optimal number (m) of apertures in an AIMD as defined supra for generating the optical energy pulse of the optimal optical power (Popt).

In a preferred embodiment, the data sent via the communication unit between the encapsulation unit and the tissue coupling unit comprises one or more of,
- from the tissue coupling unit to the encapsulation unit, including one or more of,
  - confirmation that an electrical pulse was delivered to the electrodes,
  - the values of the voltage (u) and/or the intensity (I) of the electrical pulses delivered to the electrodes measured by the sensing unit in an AIMD as described supra,
  - a value of the required optical power (Popt) of the optical energy pulse for generating the target intensity (It), in an AIMD according to claim 3,
- from the encapsulation unit to the tissue coupling unit, including one or more of,
  - the value of the target intensity (It),
  - the optimized values of Us or Up.

In a preferred embodiment, the AIMD comprises a power transfer unit for transferring power from the encapsulation unit to the tissue coupling unit, the power transfer unit comprising,
- one or more power photovoltaic cells coupled to the electrical circuit of the tissue coupling unit,
- a power light source, preferably a LED, coupled to the implanted controller enclosed in the encapsulation unit, and
- a power optical fibre different from the stimulation optical fibre and preferably different from the one or two communication optical fibres, preferably comprised in the implanted energy transfer unit, the power optical fibre comprising a proximal end coupled to the encapsulation unit in optical communication with the power light source enclosed in the encapsulation unit, and a distal end coupled to the tissue coupling unit in optical communication with the one or more power photovoltaic cells of the tissue coupling unit, for energizing the electrical circuit.

In the AIMD of the latter embodiment, the communication light source) is the same as the power light source, and the power optical fibre is the same as the single communication optical fibre or is the same as the second communication optical fibre.

The PV unit of the AIMD contains Nt PV-cells and the regulation unit is preferably configured for determining the optimized values of Us or Up with different values of N≤Nt.

BRIEF DESCRIPTION OF THE FIGURES

For a fuller understanding of the nature of the present invention, reference is made to the following detailed description taken in conjunction with the accompanying drawings in which:

FIG. 1(a): shows a general view of an opto-AIMD according to the present invention.

FIG. 1(b): shows a view of the encapsulation unit of the opto-AIMD of FIG. 1(a).

FIG. 1(c): shows a view of the energy transfer unit of the opto-AIMD of FIG. 1(a).

FIG. 1(d): shows a view of the tissue coupling unit of the opto-AIMD of FIG. 1(a).

FIG. 1(e): shows an example of stimulation pulse followed by a recovery pulse, such that |Qs|=|It×ts|≃|Qr|=|Ir×tr|, FIG. 2(a): shows a PV-unit comprising N=4 PV-cells arranged in series (Us=4, Pp=1).

FIG. 2(b): shows a PV-unit comprising N=4 PV-cells arranged in two units in parallel, each unit comprising two PV-cells in series (Us=2, Pp=2).

FIG. 2(c): shows a PV-unit configurations comprising N=4 PV-cells arranged in parallel (Us=1, Pp=4).

FIG. 3(a): shows a PV-unit configurations comprising N=6 PV-cells arranged in series (Us=6, Pp=1).

FIG. 3(b): shows a PV-unit configurations comprising N=6 PV-cells arranged in two units in parallel, each unit comprising three PV-cells in series (Us=3, Pp=2).

FIG. 3(c): shows a PV-unit configurations comprising N=6 PV-cells arranged in three units in parallel, each unit comprising two PV-cells in series (Us=2, Pp=3).

FIG. 3(d): shows a PV-unit configurations comprising N=6 PV-cells arranged in parallel (Us=1, Pp=6).

FIG. 4(a)-4(c): show an embodiment of PV-unit according to the present invention comprising N=4 PV-cells and switches allowing the values of Us and Pp to be varied such as to yield the configurations illustrated in FIGS. 2(a) to 2(c), respectively.

DETAILED DESCRIPTION OF THE INVENTION

Figure 5A:
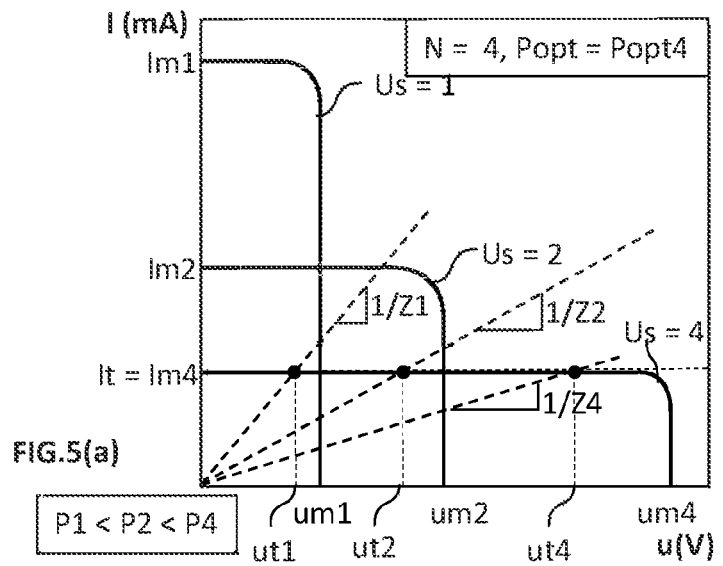
FIG. 5(a): shows an example of the I=f(u) characteristic curves characterizing a PV-unit comprising N=4 PV-cells, depending on its configuration according to FIGS. 2(a) to 2(c), with different values of the impedance (Z1, Z2, Z4); the optical power, Popt=P4, is set such that the target intensity (It) fits the I=f(u) characteristic curve, for the configuration of N=4 PV-cells arranged in series (Us=4, Pp=1).

The present invention concerns a system including an active implantable medical device (opto-AIMD) (1) configured for being implanted in a patient's body. As shown in FIG. 1(a), the AIMD comprises at least an encapsulation unit (50) suitable for being subcutaneously implanted in a body of a patient, a tissue coupling unit (60) suitable for being subcutaneously implanted and coupled to a tissue at a location separated from the encapsulation unit (50), and an implanted energy transfer unit (40) comprising a stimulation optical fibre (41s) bringing in optical communication the encapsulation unit (50) with the tissue coupling unit (60).

The encapsulation unit (50) encloses most elements required for activating the AIMD. Since in the vast majority of cases, it is too large for implanting directly adjacent to the tissue to be stimulated, the encapsulation unit is generally implanted at a location remote from the tissue to be stimulated. For example, the encapsulation unit can be implanted in a subclavian region of the patient. As shown in FIG. 1(b), the encapsulation unit (50) comprises a housing (50h) enclosing, an implanted energy pulse generator (IPG) (51) coupled to a light source (53L), for delivering optical energy pulses of optical power (Popt), a source of power (52) for activating the IPG (51) and configured for generating a battery power (Pbat) which can be varied, an implanted controller (54) configured for instructing the IPG to deliver optical energy pulses of a given optical power (Popt) as a function of time The source of power (52) can be an implanted source including for example, a battery or a supercapacitor, rechargeable or not, or it can be an external source including for example, an induction coil configured for inducing a current upon exposure to a magnetic field generated from an extracorporeal source. The latter is often implemented in cochlear implants.

The tissue coupling unit (60) is configured for being coupled directly to the tissue to be stimulated. As shown in FIG. 1(c), the tissue coupling unit (60) comprises,
- an insulating support (64) supporting,
- an electrical circuit (62) configured for delivering electrical pulses of a given target intensity (It) and comprising,
  - a photovoltaic unit (PV-unit) (61) comprising N≥2 photovoltaic (PV) cells (61p), positioned in optical contact with the distal end of the optical fibre (41s) for transforming the optical energy pulses transmitted by the optical fibre into electrical energy pulses of the target intensity (It),
  - electrical conductors for transferring the electrical energy pulses from the PV-unit to
  - electrodes (61) mounted on the insulation support (64) such as to be in electrical contact with the tissue when the insulation support is coupled to the tissue.

The tissue coupling unit (60) receives the optical energy pulses delivered by the IPG (51) of the encapsulation unit via a stimulation optical fibre (41s) belonging to the implanted energy transfer unit (40). The stimulation optical fibre (41s) comprises a proximal end optically coupled to the light source (53L), and a distal end coupled to a tissue coupling unit (60). The stimulation optical fibre (41s) is configured for transferring optical energy from the light source (53L) of the encapsulation unit (50) to the tissue coupling unit (60), As described in the Background of the Invention supra, optically transferring optical energy pulses from the encapsulation unit (50) to the tissue coupling unit (60) and transforming the optical energy pulses into electrical pulses faces numerous challenges, in particular, of energy losses along the energy transfer chain. An energy transfer chain is composed of a light source for emitting optical pulses, an optical fibre for transferring the optical pulses, and a photovoltaic (PV-) unit for transforming the optical pulses into electrical pulses for creating a current of target intensity (It) between the electrodes.

The source of power (52) supplies a battery power (Pbat) for powering the energy transfer chain of the opto-AIMD. The battery power (Pbat) can be generated by any type of source of power (52) as discussed supra, and is not restricted to a battery. Energy losses increase the consumption of battery power (Pbat) which is a major drawback for implanted AIMD's. The opto-AIMD of the present invention allows reducing battery power (Pbat) consumption required for a delivering a desired current target intensity (It) to the electrodes (65) by optimizing in situ,
- the PV-unit (61), and/or
- the light source (53L).

The gist of the present invention is that either or both PV-unit (61) and light source (53L) can be optimized with the opto-AIMD already implanted in the patient's body. This is essential, since the optical power (Popt) the light source (53L) must emit, and the target voltage (vt) the PV-unit must generate to yield the desired target current depends inter alia on the impendence (Z) measured between the electrodes (65). The value of the impedance (Z) can only be measured directly on the patient with the implanted opto-AIMD, since it depends on the type, size, and health of the tissue the electrodes (65) of the tissue coupling unit (60) are coupled to, as well as on the actual electric contact between the electrodes and the tissue obtained after the surgical implantation of the opto-AIMD. The energy transfer chain of an opto-AIMD according to the present invention can be optimized at intervals of the service life of the implanted opto-AIMD to take account of wear of the opto-AIMD and movements of the patient. To our knowledge, this is the first time a solution is proposed allowing the energy transfer chain of an implanted opto-neurostimulator to be optimized in situ and in vivo.

Optimization of the PV-Unit (61)

In a first aspect of the present invention, the energy transfer chain can be optimized in situ at the level of the PV-unit (61) to reduce the battery power (Pbat) consumption required for generating electric pulses of target intensity (It) between the electrodes (65). The PV-unit (61) of the present invention comprises N≥2 photovoltaic (PV) cells (61p). The PV-unit comprises a number, Us, of units arranged in series. Each of the Us units comprises a number, Pp, of photovoltaic cells (PV-cells) arranged in parallel. An alternative though equivalent way of defining the PV-unit of the present invention, is that the PV-unit comprises a number, Up, of units arranged in parallel. Each of the Up units comprises a number, Ps, of PV-cells arranged in series. The numbers Us, Up of units and, Pp, and Ps of PV-cells are positive natural (integer) numbers, 1, 2, 3, . . . (i.e., Us, Up, Pp, and Ps∈N), and Us×Pp=Up×Ps=N=constant. In the following, the discussion will usually use the values Us and N. The values of the other corresponding values of Up, Ps, and Pp, can unambiguously be determined through the above relation, Us×Pp=Up×Ps=N.

FIGS. 2(a) to 2(c) show the three possible configurations (Us=4, 2, or 1) of a PV-unit (61) comprising N=4 PV-cells, when all PV-cells are used. In FIG. 2(a), Us=N=4 (and Pp=1) corresponding to a configuration of the four PV-units arranged in series. In FIG. 2(c), Us=1 (and Pp=N=4) corresponding to a configuration of the four PV-units arranged in parallel. In FIG. 2(b), Us=2 (and Pp=2), with Us=2 units arranged in series, each unit comprising Pp=2 PV-cells arranged in parallel (see left hand side circuit of FIG. 2(b)). The equivalent circuit on the right hand side of FIG. 2(b) is best characterized in terms of Up=2 units arranged in parallel, each unit comprising Ps=2 PV-cells arranged in series.

Similarly, FIGS. 3(a) to 3(d) show the four possible configurations (Us=6, 3, 2, or 1) of a PV-unit (61) comprising N=6 PV-cells. In FIG. 3(a), Us=N=6 (and Pp=1) corresponding to a configuration of the six PV-units arranged in series. In FIG. 3(d), Us=1 (and Pp=N=6) corresponding to a configuration of the six PV-units arranged in parallel. FIG. 3(b) shows the configuration corresponding to Us=3 and Pp=2 with Us=3 units arranged in series, each unit comprising Pp=2 PV-cells arranged in parallel or, expressed differently, corresponding to Up=2 and Ps=3 with Up=2 units arranged in parallel, each unit comprising Ps=3 PV-cells arranged in series. Similarly, FIG. 3(c) shows the configuration corresponding to Us=2 and Pp=3 with Us=2 units arranged in series, each unit comprising Pp=3 PV-cells arranged in parallel or, expressed differently, corresponding to Up=3 and Ps=2 with Up=3 units arranged in parallel, each unit comprising Ps=2 PV-cells arranged in series.

PV-Unit (61)

As shown in FIGS. 4(a) to 4(c), the electrical circuit (62) comprises switches (S1-S6) configured for varying the values of Us and Up. The electrical circuit (62) can comprise a switch control module configured for controlling the switches yielding optimized values of Us or Up, such that the power (Popt) of the optical energy pulses required for yielding the electrical pulses of the given target intensity (It) is minimized. The switch control module changes the positions (OPEN/CLOSED) of the switches preferably according to instructions received from a regulation unit.

FIGS. 4(a) to 4(c) illustrate an embodiment of PV-cell comprising N=4 PV-cells (61p1-61p4) arranged in an electrical circuit provided with six switches (S1-S6). FIG. 4(a) illustrates a switch arrangement yielding a configuration of the N=4 PV-cells arranged in series. This corresponds to the configuration illustrated in FIG. 2(a), with Us=4 and Pp=1 (or Up=1 and Ps=4).

By switching all the switches (S1-S6) of the circuit of FIG. 4(a), a circuit as illustrated in FIG. 4(c) is obtained, wherein the N=4 PV-cells are arranged in parallel, corresponding to the configuration of FIG. 2(c) with Us=1 and Pp=4 (or Up=4 and Ps=1). FIG. 4(b) shows the switches arrangement required for yielding a circuit corresponding to the one illustrated in FIG. 2(b) with Us=2 and Pp=2 (or Up=2 and Ps=2), with Us=2 units arranged in parallel, each unit comprising Pp=2 PV-cells arranged in parallel.

The switch arrangement (OPEN/CLOSED) can be varied by the switch control module.

Optimization of Us and Pp (or Up and Ps)

The switch control module can receive instructions from the regulation unit on how the switch arrangement must be varied. The regulation unit is configured for determining the optimized values of Us or Up and can be lodged entirely in the encapsulation unit (50) or in the tissue coupling unit (60) or it may be lodged partly in the encapsulation unit and partly in the tissue coupling unit. In case the regulation unit is lodged partly or entirely in the encapsulation unit (50) a communication unit is required to transmit the instructions to the switch control module. The electrical circuit (62) may comprise a sensing unit configured for measuring values of a voltage (u) and/or an intensity (I) of the electrical pulses delivered to the electrodes. For example, a voltage comparator can be used to determine the voltage between the electrodes (65). The thus measured values of the voltage (u) and/or intensity (I) can then be used by the regulation unit for optimizing the values of Us or Up.

Figure 7:
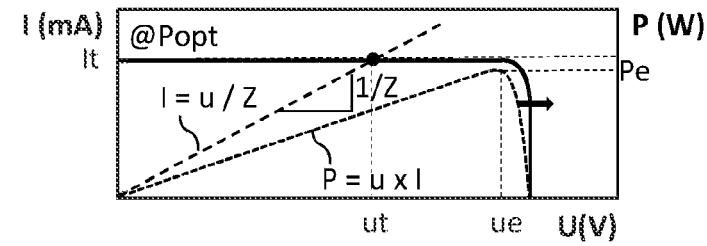
FIG. 7: shows a typical I=f(u) or (I-u) characteristic, curve of a PV-unit comprising one PV-cell or an array of PV-cells, including the I=u/Z straight line indicative of the couple (ut, It) and the curve P=u×I indicative of the efficiency of the PV-unit, and showing the values of ut and ue.

FIG. 5(a) shows an example of performance graphs of a PV-unit (61) comprising N=4 PV-cells depending on the values of Us. The performance graphs show the current intensity (I) as a function of the voltage (u) that a PV-unit (61) can generate depending on the configuration of the PV-cells (61p) in the PV-unit (61). The intensity must be equal to the target intensity (It) which is generally defined by a medical practitioner. It can be seen in FIG. 5(a) that the performance of the PV-unit (61) varies substantially depending on the configuration of the PV-cells (i.e., of the value of Us). For example, the PV-unit characterized by Us=4 (i.e., all N=4 PV-cells are arranged in series) yields the largest voltage (u) for a low intensity (I). Referring to FIG. 7 and the discussion thereon in the Background of the Invention supra, the PV-unit (61) should be used at or as close as possible to the optimal efficiency of the PV-unit, such that the target voltage (ut) is equal or close to and smaller than the maximum efficiency voltage (ue) (i.e., ut≃ue). This configuration of Us=N=4 is therefore quite suitable for opto-AIMD's implanted in a patient generating a high value of the impedance (Z=Z4), since the target voltage (ut) required for yielding the target intensity (It) is defined as |ut|=|Z|×|It|(cf. straight dashed line of slope 1/Z4 in FIGS. 5(a) and 5(d)).

By contrast, the PV-unit characterized by Us=1 (i.e., all N=4 PV-cells are arranged in parallel) yields the lowest voltage (u) for a current of higher intensity (I). This configuration is quite suitable for opto-AIMD's implanted in a patient generating a low value of the impedance (Z=Z1), since the target voltage (ut) required for yielding the target intensity (It) is defined as |ut|=|Z|×|It|(cf. straight dashed line of slope 1/Z1 in FIGS. 5(a) and 5(b)).

Finally, intermediate voltage (u) and intensity (I) are obtained with a configuration of Us=2. This configuration is therefore quite suitable for opto-AIMD's implanted in a patient generating an intermediate value of the impedance (Z=Z2).

Optimization of Us as a Function of Z, Using all PV-Cells of the PV-Unit (N=Nt)

The PV-unit is formed of a number Nt of PV-cells and the invention aims to determine the optimized value of Us with N PV-cells, wherein N≤Nt. In the present section, a first embodiment is addressed, wherein the optimized value of Us is determined for a number N of PV-cells equal to Nt, i.e., all the PV-cells of the PV-unit are necessarily used.

In one embodiment illustrated in FIGS. 5(a) to 5(d), the regulation unit is configured for determining the optimized values of Us (or Up), as follows,
    for a given value of the optical power (Popt), determining or measuring a target voltage (ut) corresponding to the target intensity (It) when the opto-AIMD is implanted with the tissue coupling unit (60) coupled to a tissue (a voltage comparator can for example be used),
    determining an optimal value of Us (or Up) yielding a maximum voltage (um1, um2, um4) which is larger than, and the closest to the value of the target voltage (ut),
    adjusting the power (Popt) of the optical energy pulses to an optimal optical power (Popt1, Popt2, Popt4) required to reach the target intensity (It) with the optimal value of Us (or Up) determined in the preceding step.

In a first embodiment, the determination or measurement of the target voltage (ut) can be carried out by generating and transmitting optical pulses of a given optical power (Popt) known to yield upon irradiation of the PV-unit with Us=N (or Up=1), a current of the target intensity (It), and measuring or determining a voltage between the electrodes (61) which corresponds to the target voltage (ut), In a second embodiment, the determination or measurement of the target voltage (ut) can be carried out as follows. Irradiating the N PV-cells (61p) of the PV-unit arranged in series (i.e., Us=N) with a light beam of any given value of the optical power (Popt) (preferably the value of Popt yielding the target intensity (It) for Us=N) and with Us=N, measuring a voltage (u) and an intensity (I) between the electrodes (61),
    determining an impedance (Z) with |Z|=|u|/|I| and
    calculating the target voltage (ut) with |ut|=|Z|×|It|.

Referring to FIG. 5(a), the PV-unit was irradiated with an optical power (Popt) known to yield the target intensity (It) with the N=4 PV-cells arranged in series (i.e., curve labelled Us=4). The impedance (Z) is then measured or determined. Three examples of impedances (Z1<Z2<Z4) are illustrated in FIG. 5(a) with a high impedance (Z4) yielding a low value of the slope 1/Z4 of the I=u/Z straight line, a low impedance (Z1) yielding a high value of the slope 1/Z1, and an intermediate impedance (Z2) yielding an intermediate value of the slope 1/Z2.

The values of the corresponding target voltages (ut1, ut2, ut4) either measured directly at the electrodes (65) or calculated, can be determined arithmetically or graphically at the intersection points (illustrated by black dots in FIG. 5(a)) of the I=u/Zi straight lines (i=1, 2, or 4) with the (I-u) characteristic curve of the PV-unit with Us=4, The optimal value of Us requiring the lowest value of optical power (Popt) to generate the target intensity (it) is the value of Us corresponding to a PV-cells (61p) arrangement characterized by an actual power (P1, P2, P4) measured at the target voltage (ut1, ut2, ut4), which is closest to the corresponding power of maximum efficiency (Pe) of the corresponding PV-unit configurations, i.e., the difference ($\Delta Pe=Pe-Pi$, i=1, 2, 4) between the power of maximum efficiency (Pe) and the actual powers delivered by the PV-unit at the target voltages (P1, P2, P4) is the smallest. $\Delta Pe$ can be defined as the efficiency loss relative to the power of maximum efficiency (Pe) and must be minimized. It is preferred that the optimal value of Us yields an actual power (P1, P2, P4) of at least 70%, preferably at least 80%, more preferably at least 90% of the power of maximum efficiency (Pe) for the corresponding values of the impedance (Z) measured on an implanted patient.

Figure 5B:
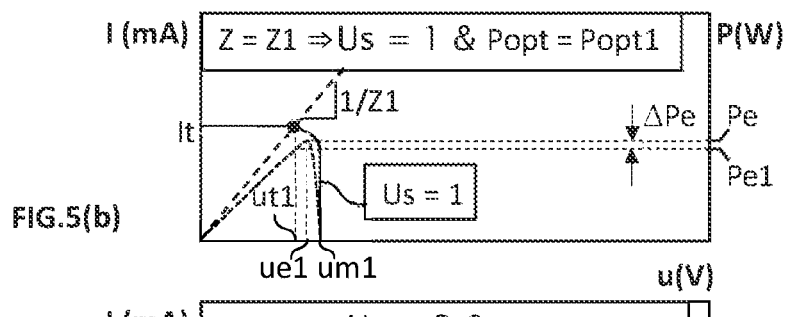
FIG. 5(b): shows an optimized PV-unit configuration for an impedance Z1.
Figure 5C:
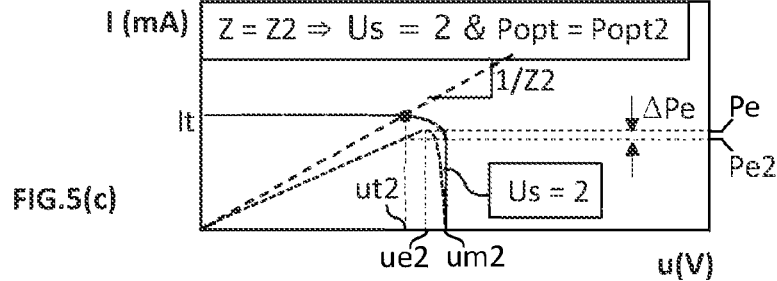
FIG. 5(c): shows an optimized PV-unit configuration for an impedance Z2.
Figure 5D:
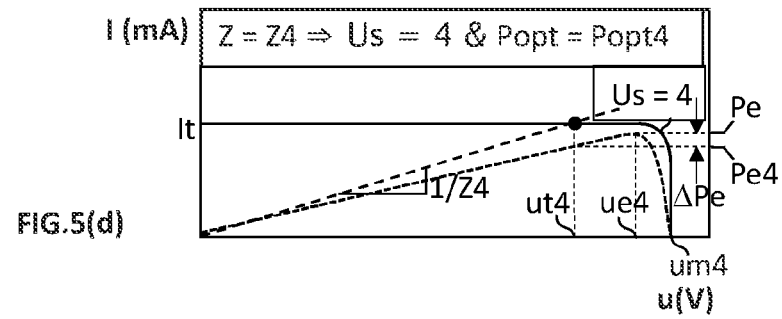
FIG. 5(d): shows an optimized PV-unit configuration for an impedance Z4.

It is therefore a necessary condition that the target voltage (ut1, ut2, ut4) be smaller than the maximum voltage (um1, um2, um4) that a given PV-unit configuration can generate (cf. FIG. 5(a)), since in such configuration, the PV-unit cannot generate the target current (It) at voltages higher than the corresponding maximum voltage (um1, um2, um4). For example, if the impedance is Z=Z4 (cf. curve of slope 1/Z4 in FIG. 5(a)), only an arrangement of N=4 PV-cells in series can be used to generate the target intensity (It). For this reason, FIG. 5(d) illustrates graphically that, for an impedance Z=Z4, the optimal value of Us is Us=4 PV-cells in series. The optical power (Popt) needs not be varied, since it was first set to yield the target intensity (It) for that configuration.

It can be appreciated from FIG. 5(a) that the configuration of N PV-cells arranged in series (i.e., Us=N) is capable of generating the target intensity for all the measured values of the impedance (Z1, Z2, Z4). This explains that a state-of-the-art opto-AIMD with all PV-cells of the PV-unit arranged in series (i.e., Us=N) can be implanted in any patient having an impedance lower than or equal to Z4. The target voltages (ut1, ut2) for low to moderate values of the impedance (Z1, Z2) are, however, far remote from the maximum efficiency voltage (ue4) (compare FIGS. 5(b) and 5(c) with FIG. 5(d)). Consequently, a value of Us=4 would appear as sub-optimal for low to moderate values of the impedance of Z1 or Z2, thus requiring a higher optical power (Popt) than necessary for generating a current of target intensity (It). Optimization of the value of Us is thus required to lower the battery power (Pbat) consumption of the opto-AIMD.

The values of the maximum efficiency voltage (ue1, ue2, ue4) yielding the powers of maximum efficiency (Pe) of a PV-unit for different values of Us are known from the supplier. The regulation unit can be configured for comparing the value of the target voltage (ut1, ut2, ut4) with the curves of the efficiency voltage and determining the corresponding values of actual power (Pe1, Pe2, Pe4) at the target voltage (ut1, ut2, ut4). The optimal value of Us is the value defining the configuration yielding the highest value of efficiency (smallest value of $\Delta Pe=Pe-Pei$, with i=1, 2, or 4), i.e., the value which is closest to the corresponding values of the powers of maximum efficiency (Pe).

Alternatively, the optimal value of Us can be determined without measuring the impedance (Z) as follows. The regulation unit can switch to various values of Us and measure the intensity of the current thus generated for each value of Us. This process aims at iteratively determining the value of Us yielding a maximum voltage value (um1, um2, um4) which is larger than and closest to the value of the (unknown) value of the target voltage (ut) and which generates the current of target intensity (It). For example, one can start with the configuration defined by Us=1 (i.e., N PV-cells in parallel), which yields the lowest value of the maximum voltage (um1) and measure the current intensity generated between the electrodes (65) upon irradiation of the PV-unit (61) by an optical power (Popt). If a current of target intensity (It) is measured, it can be concluded that the target voltage is smaller than the corresponding maximum voltage of the (I-u) characteristic curve, with Us=1 (i.e., ut<um1), without measuring the actual value of ut, or of Z, used to determine ut=Z×I. Since the maximum voltage (um1) of an arrangement of N PV-cells arranged in parallel (i.e., Us=1, or Up=N) is the smallest possible value of the maximum voltage (um1, um2, um4), the PV-unit cannot be further optimized than by selecting Us=1. This would be the case in FIGS. 5(a) and 5(b) if the measured impedance (Z) was equal to Z1 (i.e., a low value of impedance, with Z1<Z2<Z4).

If, on the other hand, the current generated has an intensity smaller than the target intensity (It) (i.e., I<It) with the PV-cell configuration, Us=1), it can be concluded that the target voltage (ut) is higher than the maximum voltage (um1) of the PV-unit with N PV-cells in parallel (i.e., ut>um1 at Us=1). In this case, the PV-cell configuration of Us=1 or Up=N cannot be used to generate the target intensity (It) because the impedance (Z) is too high for this PV-cells configuration. An alternative configuration or value of Us characterized by a higher value of the maximum voltage (um2, um4) must be tested by the regulation unit.

The regulation unit instructs the switch control to switch to a configuration with 1<Us≤N, which yields the second lowest value of maximum voltage (um2), the lowest value being um1 corresponding to Us1 (=N PV-cells arranged in parallel).

As illustrated in FIGS. 2(b), 4(b), 5(a), and 5(c), for N=4 PV-cells, there is only one configuration left other than Us=1 and Us=4, namely Us=2. For N>4, there can be more configurations available between Us=1 and Us=N. The number of configurations as a function of N is determined by the relation, Us=N/Pp, wherein Us, Pp, and N∈N. For example, as shown in FIGS. 3(a) to 3(d), for N=6 PV-cells, there are two more configurations comprised between Us=1 and Us=N=6, namely Us=2, and Us=3, illustrated in FIGS. 3(b) and 3(c), respectively. Similarly, if N=12, there can be several values of Us comprised between 1 and 12, namely, 2, 3, 4, and 6. For sake of clarity and conciseness, the following steps are described for N=4. A skilled person can easily extrapolate the method for different values of N. The available values of Us are listed in Table 1 as a function of the values of N. The corresponding numbers of available values of Us are also indicated in Table 1.

If it was concluded that the maximum voltage (um2) for Us=2 is smaller than the target voltage (ut), (i.e., um2<ut) then the same operation is repeated with a different value of Us, and the current intensity generated between the electrodes (65) is measured upon irradiation of the PV-unit (61) with the configuration yielding the second lowest value of the maximum voltage, viz., for N=4, this corresponds to Us=2. If a current is measured, it can be concluded that the target voltage is smaller than the corresponding maximum voltage of the (I-u) characteristic curve, with Us=2 (i.e., um1<ut<um2). The regulation unit can thus conclude that the optimal PV-unit configuration available for N=4 PV-cells and an impedance Z2 is Us=2. This case is illustrated in FIGS. 5(a) and 5(c) with the measured impedance (Z) equal to Z2 (i.e., an intermediate value of impedance Z2, with Z1<Z2<Z4).

If, on the other hand, the current thus generated has an intensity lower than the target intensity (i.e., I<It), it can be concluded that the target voltage (ut) is higher than the maximum voltage (um2) of the PV-unit with N=4 PV-cells at Us=2, ut>um2). In this case, the PV-cell configuration of Us=2 cannot be used to generate the target intensity (It) because the impedance (Z) is too high. This would be the case in FIGS. 5(a) to 5(d) if the measured impedance (Z) was equal to Z4 (i.e., a high value of impedance Z4, with Z1<Z2<Z4). The regulation unit instructs the switch control to switch to a configuration with 1<Us≤N, which yields the third lowest value of maximum voltage (um4), since the values of the maximum voltages (um1, um2) corresponding to the configurations Us+1 and 2, respectively, were too low and unable to generate the target intensity (It) because an excess of impedance leads to voltage saturation. For N=4, the third value of um is um4 corresponding to the configuration of Us=4, with all 4 PV-cells arranged in series. After testing, if a current of target intensity (It) is measured, then Us=4 is the optimal value of Us, and if a current of intensity lower than the target intensity (It) is measured, then there is a problem. The absence of current could be explained by an injured or dysfunctioning tissue, or by a problem with the AIMD such as a damaged optical fibre or with the electrical contact between the electrodes (65) and the tissue to be stimulated. For other values of the number (N) of PV-cells, see Table 1.

TABLE 1

Values and number of values of Us as a function of N if all N PV-cells are used (N = Nt) if a portion N only of the Nt PV-cells available in the PV-unit is used (N < Nt).

| | N = Nt | | N ≤ Nt [(1)] | | | |
|---|---|---|---|---|---|---|
| N | Us Pp = N/Us | Nb Us-values | N | Us | Pp | Nb Us-values |
| 2 | 1, 2 | 2 | 2 | | | 2 |
| 3 | 1, 3 | 2 | 3 | | | 2 |
| 4 | 1, 2, 4 | 3 | 4 | | | 3 |
| 5 | 1, 5 | 2 | 5-4 | 1, 5-2 | 5, 1-2 | 3 |
| 6 | 1, 2, 3, 6 | 4 | 6 | 1, 2, 3, 6 | 6, 3, 2, 1 | 4 |
| 7 | 1, 7 | 2 | 7-6 | 1, 7-2, 3 | 7, 1-3, 2 | 4 |
| 8 | 1, 2, 4, 8 | 4 | 8 | 1, 2, 4, 8 | 8, 4, 2, 1 | 4 |
| 9 | 1, 3, 9 | 3 | 9-8 | 1, 3, 9-2, 4 | 9, 3, 1-4, 2 | 5 |
| 10 | 1, 2, 5, 10 | 4 | 10-9 | 1, 2, 5, 10-3 | 10, 5, 2, 1-3 | 5 |
| 11 | 1, 11 | 2 | 11-10, 9 | 1, 11-2, 3, 5 | 1, 2 | 5 |
| 12 | 1, 2, 3, 4, 6, 12 | 6 | 12 | 1, 2, 3, 4, 6, 12 | 1, 3 | 6 |

[(1)] Only values with N < Nt yielding a reduced optical power (Popt) consumption for generating the target intensity (It).

Once the optimal value of Us has been determined, the optical power (Popt=Popt1, Popt2, or Popt4) can be adapted to yield the target intensity (It) with said PV-cell configuration. This is illustrated in FIGS. 5(b) to 5(d) for values of the impedance Z1, Z2, and Z4, respectively at Us=1, Us=2, and Us=4, respectively.

Table 2 reveals the optimization potential of an opto-AIMD according to the present invention compared with a state-of-the-art opto-AIMD with a single PV-unit configuration of Us=N PV-cells arranged in series dimensioned for being operational with high values (Z4) of the impedance. The following discussion is illustrated with N=4 PV-cells. It is clear that the same conclusions can be extrapolated to different values of N.

If the impedance measured on a first patient is high (Z4 in FIGS. 5(a) and 5(d) and Table 2), then the PV-unit (61) takes the configuration Us=N=4, which corresponds to the single PV-unit configuration of the state-of-the-art opto-AIMD. The same optical power (P4) will be required to generate the target intensity (It) with the state-of-the-art opto-AIMD as with the opto-AIMD of the present invention, yielding the same battery power (Pbat) consumption. A ratio (PoptINV/PoptPA) of the optical power (PoptINV) of the opto-AIMD of the present invention to the optical power (PoptPA) of the state-of-the-art opto-AIMD is therefore 100%. The two types of opto-AIMD's work in similar conditions.

The measured impedance (Z), however, is statistically seldom as high as or higher than Z4. This is explained because to ensure that a given opto-AIMD model can be used in as many patient cases as possible (i.e., "one fits them all"), the producer must dimension the opto-AIMD to be operational for values of Z substantially higher than average, since for higher values of the impedance a current of intensity lower than the target intensity is generated by the PV-unit (i.e., Z>Z4⇒I<It). This is illustrated in FIG. 5(g), showing the probability density (solid curve, left-hand ordinate) and cumulative density (dashed curve, right-hand ordinate), wherein a large proportion of the implanted patients (e.g., at least 90%) yield a measured impedance value lower than the high impedance value (Z4) (cf. FIG. 5(g)). For the less than 10% of patients showing an impedance value greater than Z4, it should be investigated whether such high value of the impedance is due (a) to the nature and condition of the tissue to be stimulated (e.g., an injured or dysfunctioning tissue), (b) to the quality of the electrical contact between the electrodes (65) and the tissue to be stimulated, (c) to a defect in the energy transfer chain causing important energy losses between the light source (53) and the electrodes, or (d) other defects of the opto-AIMD. The same probability density of FIG. 5(g) can be applied to the values of the target intensity, with 90% of the patients being prescribed a target intensity lower than a high value of the target intensity, and only about 10% requiring pulses of intensity higher than the high value of the target intensity.

For a vast majority of patients, the impedance (Z) is smaller than the high value (Z4) the state-of-the-art opto-AIMD was designed for (i.e., Z1, Z2<Z4), and the single PV-unit configuration of Us=N PV-cells arranged in series of the state-of-the-art opto-AIMD becomes sub-optimal for impedance values lower than the high value Z4, because requiring a higher optical power (Popt=P4) than for alternative PV-unit configurations to generate the same target intensity (It). Referring to FIGS. 5(a) and 5(c) and to Table 2, if the impedance measured on a second patient is Z2<Z4, yielding a value of the target voltage (ut2) smaller than the maximum voltage (um2) of a PV-unit configured with Us=2, then the same N=4 PV-cells arranged in two units arranged in series, each unit comprising two PV-cells arranged in parallel (cf. FIGS. 2(b) and 4(b)) would generate a current of intensity about twice as high as the target intensity (Im2≃2 Im1=2 It) upon irradiation with an optical beam of optical power Popt=P4 (cf. FIG. 5(a)). This means that by switching the PV-unit from a state-of-the-art single configuration Us=N with all N PV-cells arranged in series to a mixed configuration with Us=2 with units is series of parallel PV-cells, the optical power (Popt) can be reduced accordingly to a value Popt=Popt2≃Popt4/2, to yield the target intensity (It). This results in substantial reduction of battery power (Pbat). The ratio PoptINV/PoptPA drops to approximately 50% (cf. Table 2).

TABLE 2

Comparison of optical power (Popt) required for generating
It as a function of Z, with state-of-the-art opto-AIMD's
and opto-AIMD according to the present invention.

| N = 4 | State of art opto-the AIMD | | opto- INV AIMD | | Saving (PoptINV-PoptPA)/PoptPA |
|---|---|---|---|---|---|
| Z | Us | PoptPA | Us | PoptINV | |
| Z4 | 4 | Popt4 | 4 | Popt4 | 0% |
| Z2 | 4 | Popt4 | 2 | Popt2 ≃ Popt4/2 | ≃−50% |
| Z1 | 4 | Popt4 | 1 | Popt1 ≃ Popt4/4 | ≃−75% |

Z1 < Z2 < Z4

Similarly, if a low impedance Z1 is measured on a third patient with Z1<Z2<Z4, yielding a value of the target voltage (ut1) smaller than the maximum voltage (um1) of a PV-unit configured with Us=1 (i.e., all N PV-cells arranged in parallel), then the same N=4 PV-cells arranged in parallel (cf. FIGS. 2(c) and 4(c)) would generate a current of intensity about four times as high as the target intensity (Im4≃4 Im1=4 It) upon irradiation with an optical beam of optical power Popt=P4 (cf. FIG. 5(a)). This means that by switching the PV-unit from a state-of-the-art single configuration Us=N PV-cells in series to a mixed configuration with Us=1 (i.e., all N PV-cells in parallel), the optical power (Popt) can be reduced accordingly to a value Popt=Popt1≃Popt4/4, to yield the target intensity (It). This results in substantial reduction of battery power (Pbat). The ratio PoptINV/PoptPA drops to approximately 25%, corresponding to about 75% reduction in battery power (Pbat) consumption (cf. Table 2). It can be concluded that, depending on the value of the impedance (Z) measured on an implanted patient, the optical power (Popt) required for generating the target intensity (It) can vary by an order N by selecting the optimal value of Us, between a value (Poptn) at Us=N and a value (Popt1) of approximately Popt1≃Poptn/N at Us=1.

Optimization of Us as a Function of Z, Using all or Part of the PV-Cells of the PV-Unit (N≤Nt)

In the previous section, the determination of Us was discussed when all the Nt PV-cells of the PV-unit were systematically used to transform optical power (Popt) into electrical current of target intensity (It) (i.e., N=Nt). Surprisingly, in some cases, it may be advantageous to shut down one or more of the Nt PV-cells forming the PV-unit and to use instead only N PV-cells, wherein N<Nt. Such counter-intuitive configuration becomes interesting if the loss of intensity (I) or voltage (u) caused by using one or more PV-cells less than available in the PV-unit is compensated by the gain obtained with an additional configuration made available by using N PV-cells instead of all Nt PV-cells.

Figure 5E:
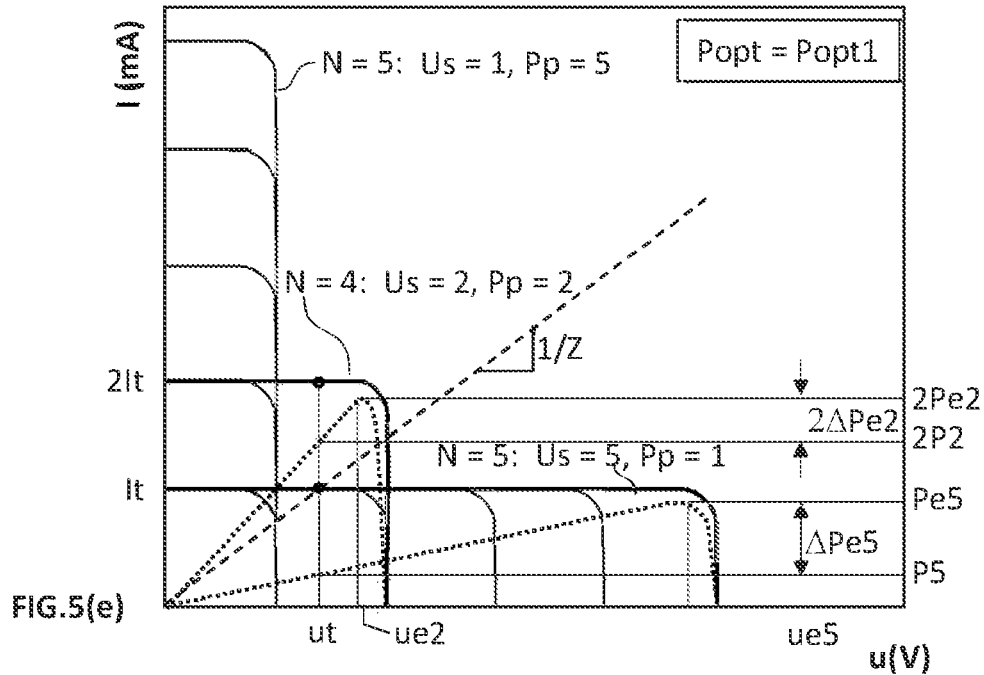
FIG. 5(e): shows an example of the I=f(u) or (I-u) characteristic curve, curves wherein it is advantageous to use only a portion N of the Nt PV-cells to save Popt, with Nt=5 and N=4.

FIG. 5(e) shows an example of (I-u) characterizing curves of different configurations of a PV-unit comprising Nt=5 PV-cells. Referring to Table 1 (left) supra, When N=5, two configurations only are available, namely Us=1 (i.e., 5 PV-cells in parallel) and Us=5 (i.e., 5 PV-cells in series). These two configurations are identified in FIG. 5(e) with the labels starting with "N=5". For an implanted patient yielding an impedance (Z) as illustrated in FIG. 5(e), long-dashed line, a current of target intensity (It) can be created with a corresponding voltage (ut), generating an actual power (P5), which is quite low, with a high value of ΔPe5=Pe5−P5, wherein Pe5 is the power of maximum efficiency for Us=5. It is clear that the configuration Us=1 with all Nt=5 PV-cells are arranged in parallel cannot create a current of target intensity (It) as voltage saturation is reached.

Figure 5F:
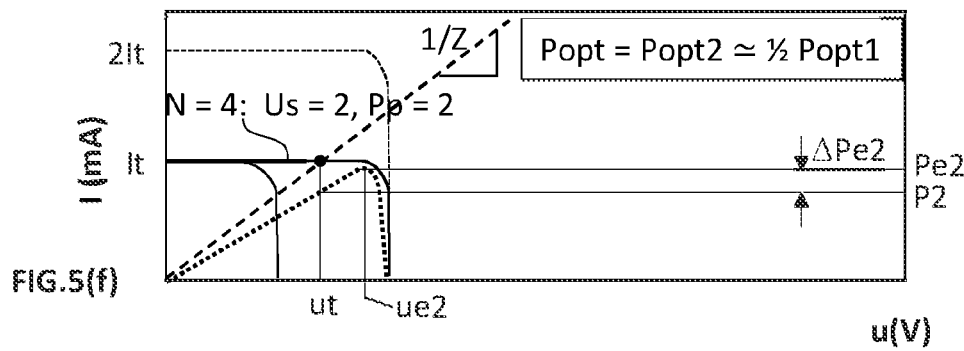
FIG. 5(f): shows how the optical power (Popt) can be reduced by selecting Us=2, Pp=2 with the PV-cell containing Nt=5 PV-cells characterized in FIG. 5(e).
Figure 5G:
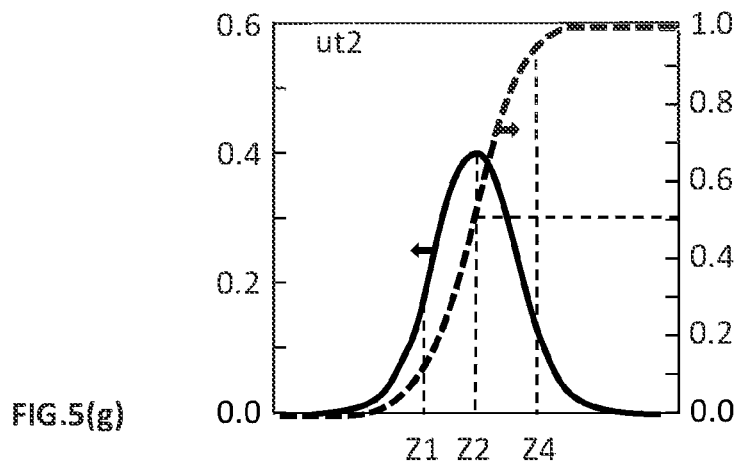
FIG. 5(g): shows an example of density distribution of the values of the impedance (Z) measured in a population of implanted patients.

By making without one of the Nt=5 PV-cells available in the PV-unit and using only N=4 PV-cells instead, it is possible to reach an additional configuration of Us=2 and Pp=2 which was not available with N=5 PV-cells. FIG. 5(e) shows that with the optical power (Popt=Popt1) a current of intensity, I=2 It, can be created with this configuration with a higher efficiency. As explained supra and illustrated in FIG. 5(f), the optical power (Popt=Popt1) can be divided by approximately 2 to create a current of target intensity (It) with a substantially lower efficiency loss ΔPe2 than with the configuration Us=5 (i.e. ΔPe2<ΔPe5). This gain of efficiency allows the optical power (Popt) to be divided by approximately 2 in spite of using one PV-cell less than actually available in the PV-unit (in this example, N=4<Nt=5).

Table 1 (right) lists the Us and Up configurations as well as the number of possible configurations available when N≤Nt. Only the configuration of N<Nt yielding additional configurations allowing saving of optical power (Popt) for some values of the impedance (Z) are listed. These are characterized by the figures following the hyphen (-) in each column.

Optimization of the values of Us and Pp as discussed supra can therefore also include determining the best value of the N PV-cells out of the Nt PV-cells available in the PV-unit to yield the most advantageous values of Us and Pp, i.e., which results in the lowest optical power (Popt) required for generating a current of the target intensity (It). The switches configuration of the PV-unit can therefore allow isolating one or more (=Nt−N) PV-cells from the rest of the Nt PV-cells, depending on the value of Nt (cf. Table 1, right). The switch control module can thus receive instructions from the regulation unit to isolate or masking (Nt−N) PV-cells to reach a number N of PV-cells affording configurations Us and Pp not available with the Nt PV-cells and which can be advantageous. The optimal values of Us and Up can be carried out as described supra, with different values of N≤Nt.

Optimization of the Light Source (53)

In a second aspect of the present invention, the energy transfer chain can be optimized in situ at the level of the light source (53) to reduce the battery power (Pbat) consumption required for generating electric pulses of target intensity (It). It has been discussed sura that the value of the optical power (Popt) required for generating the target intensity (It) could vary considerably with an AIMD according to the present invention, depending on the value of the measured impedance (Z).

Furthermore, and regardless of whether the opto-AIMD is capable or not to optimize the PV-unit as discussed supra, the optical power (Popt) to be generated by the light source (53) may vary over a broad range. As discussed in the section Background of the Invention supra with reference to FIG. 1(e), to avoid accumulation of charges in the tissues of the patient, it is preferred to send a recovery pulse of recovery intensity (Ir) for a recovery time (tr) after having sent a stimulation pulse of target intensity (It) for a stimulation time (ts), such that It×ts≃(Ir×tr). It is preferred to generate the stimulation pulses and recovery pulses from the same source of light (53) to avoid duplication of transfer energy chains. A ratio (|Ir/It|=ts/tr) of the recovery intensity (Ir) to the target intensity (It) can be of the order of 1/2 to 1/5. Applying stimulation pulses and recovery pulses with a single energy transfer chain therefore requires a source of light (53) capable of generating an optical power (Popt) varying over a range of |Ir/It| which can be of the order of 1/5.

State-of-the-art opto-AIMD's are equipped with a conventional light source. A conventional light source is a single optical emitter or a non-addressable optical emitter array. Typically an optical emitter can be a light emitting device (LED) or a laser source (e.g., VCSEL) and is capable of generating the required value of optical power (Popt) comprised within the foregoing ranges by simply varying the battery power (Pbat) fed to the light source (53). In many cases, the battery power (Pbat) consumed by conventional optical sources varies substantially linearly with the optical power (Popt) to be generated until reaching a maximum power where linearity is lost but requires a threshold battery power (Pth) to start emitting linearly. It is, however, possible to reduce the battery consumption to less than linearly proportional with the generated optical power (Popt) by using as light source (53) an addressable optical emitters array instead of the conventional single optical emitters or non-addressable optical emitter arrays.

Figure 6A:
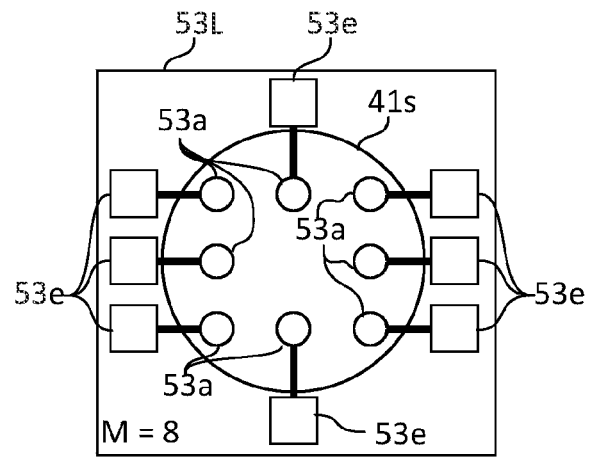
FIG. 6(a): shows a VCSEL array comprising M=8 apertures addressable independently one by one.

As illustrated in FIG. 6(a), an addressable optical emitters array comprises M>1 apertures (53a) addressable independently one by one or by sub-groups of apertures. For example, each aperture (53a) or group of apertures (53a) can be controlled independently by an electrical contact (53e). The addressable optical emitters array is preferably an array of addressable laser emitter diodes, more preferably of vertical cavity surface-emitting laser (VCSEL). It can also be an array of addressable light emitting diodes (LED). An example of addressable VCSEL array is described e.g., in U.S. Pat. No. 5,325,386.

Figure 6B:
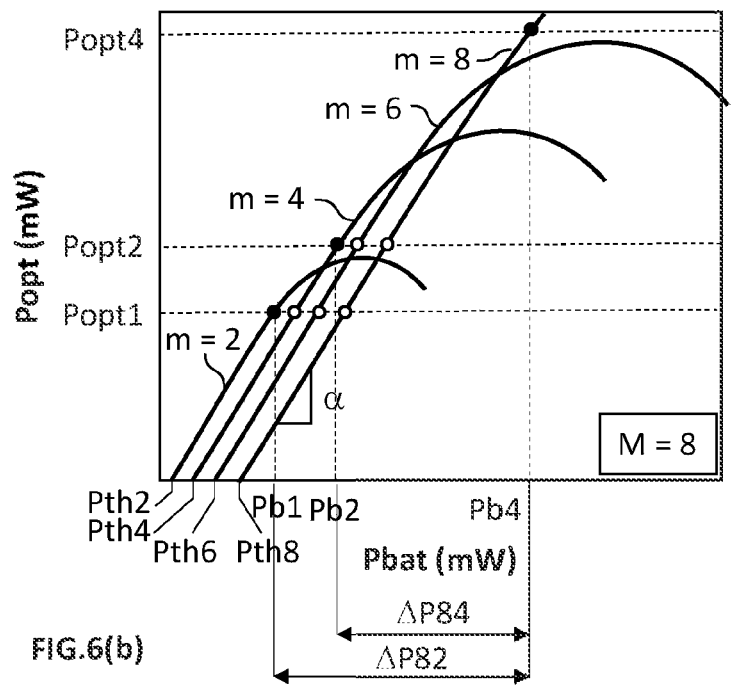
FIG. 6(b): shows the battery power (Pbat) consumption of the VCSEL of FIG. 6(a) for emitting an optical pulse of optical energy (Popt) as a function of the number m of addressed apertures. The black dots indicate the most efficient VCSEL configuration (value of m) for different values (Popt1, Popt2, Popt4) of the optical power (Popt).

FIG. 6(b) illustrates the battery power (Pbat) required for generating an optical power (Popt) for different values (m=2, 4, 6, and 8) of the number (m) of apertures addressed in combination of an array of M=8 addressable VCSEL's. Each time an aperture is addressed, a threshold battery power must be supplied to the VCSEL array to activate the corresponding laser. Once the corresponding m lasers are activated, the VCSEL array generates a light of optical power (Popt) which increases substantially linearly with the battery power (Popt) supplied to the VCSEL array, until an upper limit where the straight-line curves down. If the optical power (Popt) to be generated is higher than the upper limit of m apertures, then an additional aperture or group of apertures must be addressed to increase the number (m+1) of apertures addressed simultaneously and thus increasing the corresponding upper limit of the optical power reachable with (m+1) addressed apertures to a value higher than the desired value of Popt (=Popt1, Popt2, Popt4).

A conventional LED or laser (i.e., not an addressable array) would display a battery power (Pbat) consumption similar to the case wherein all m=M=8 apertures are addressed simultaneously, with a corresponding threshold battery power threshold value (Pth8). It can be seen in FIG. 6(b) that, for an optical power (P4) required for generating the target intensity with a measured high value (Z4) of the impedance as discussed supra with respect to FIGS. 5(a) to 5(d), all m=M=8 apertures must be addressed simultaneously resulting in a battery power (Pbat) consumption similar to the one required by a conventional laser such as a VCSEL and some types of LED's. For lower values of the optical power (Popt=Popt1 or Popt2<Popt4), it can be seen that less battery power (Pbat) is required by addressing m=2 or m=4 apertures only, rather than addressing all m=M=8 apertures. As illustrated in FIG. 6(b), a threshold battery power value (Pth) of the battery power (Pbat) is required to activate a laser each time an aperture or group of apertures is addressed. The threshold battery power value (Pth) corresponds to a threshold intensity (Ith) which, for a VCSEL, may be in the range of 0.5 to 2 mA/aperture, for example of the order of 0.6 or 0.7 mA/aperture for each additional aperture being addressed. The threshold value explains the shift of the curves each time the number (m) of addressed apertures is increased. Some VCSEL's can have higher values of the threshold intensities such as up to 10 to 20 mA/aperture and even higher.

The shift towards higher values of the battery power (Pbat) of the curves in FIG. 6(b) as the number (m) of addressed apertures (53a) increases calls for an optimization of the number (m) of apertures addressed in combination. The black dots indicate the numbers (m) of apertures to be addressed for generating a given value of the optical power (Popt=Popt1, Popt2, or Popt4) requiring the lowest battery power (Pbat). The same optical power (Popt=Popt1, Popt2, or Popt4)) can be generated with a different number (m) of apertures, indicated with the white dots, but they require a higher battery power (Pbat) for generating the same optical power (Popt) than with the numbers (m) indicated by the black dots. If the threshold current, Ith=0.6 mA/aperture, the battery must provide a threshold current of about Ith=2× 0.6=1.2 mA to start activating m=2 apertures and a threshold current of about Ith=8×0.6=4.8 mA to activate m=8 apertures. If the optical power (Popt) to be generated in low (=Popt1), addressing m=2 apertures only (cf. black dot) would consume 3.6 mA less than if all m=M=8 apertures are addressed in combination (cf. right-hand side white dot at Popt=Popt1). This corresponds to the battery power difference ΔP82 illustrated in FIG. 6(b). If the optical power Popt=Popt2 to be generated is higher than the optical power that m=2 apertures can generate, then additional apertures must be addressed. In FIG. 6(b), m=4 apertures are optimal for generating an optical power, Popt=Popt2. For generating an optical power Popt4>Popt2>Popt1, m=8 apertures can be addressed, consuming the same battery power (Pbat) as a conventional LED or laser used in state-of-the-art AIMD's.

TABLE 3

Comparison of battery power (Pbat) required for generating different values of optical power (Popt), with state-of-the-art opto-AIMD's and opto-AIMD according to the present invention.

| M = 8 | State of art opto-the AIMD | | Opto-AIMD INV | | Saving |
|---|---|---|---|---|---|
| Popt | m | PbatPA | m | PbatINV | PbatINV-PbatPA |
| Popt4 | 1 (≙8) [1] | Pth8 + α Popt4 | 8 | Pth8 + α Popt4 | Pth8 − Pth8 = 0 |
| Popt2 | 1 (≙8) [1] | Pth8 + α Popt2 | 4 | Pth4 + α Popt2 | ½ Pth8 − Pth8 = −½ Pth8 [2] |
| Popt1 | 1 (≙8) [1] | Pth8 + α Popt1 | 2 | Pth2 + α Popt1 | ¼ Pth8 − Pth8 = −¾ Pth8 [2] |

Popt1 < Popt2 < Popt4

[1] 1 (≙8) = α single aperature of a state-of-the-art VCSEL corresponds to m = M = 8 addressed aperatures of a VCSEL array of M = 8 aperatures.
[2] Pth8 = 2 Pth4 = 4 Pth2

Table 3 compares the battery power (PbatPA) consumption of a state-of-the-art opto-AIMD using a conventional source of light (LED or VCSEL) with the battery power (PbatINV) consumption of an opto-AIMD according to the present invention provided with an addressable array of VCSEL's comprising M=8 apertures (53a) for generating a high value (Popt4) an intermediate value (Popt2) and a low value (Popt1) of optical power (Popt). It is assumed that the conventional single aperture VCSEL of the state-of-the-art opto-AIMD requires a threshold power (Pth8) for activating the VCSEL which is equal to the threshold power (Pth8) required for activating all M=8 apertures of the VCSEL array of the opto-AIMD according to the present invention, of equivalent power as the former. Once the light source is activated with the corresponding threshold power (Pth), the optical power increases linearly with the battery power (Pbat) with a proportionality factor ($\alpha$). It can be seen that for generating a high value of optical power (Popt=Popt4) the VCSEL array of the present invention requires the same battery power (PbatINV) as the single LED or VCSEL of the state-of the-art AIMD (PbatPA), with PbatINV≃PbatPA. For generating lower values of optical power (Pbat=Popt1 or Popt2<Popt4), however, the opto-AIMD of the present invention allows substantial battery power saving by selecting an optimal value of the number (m) of apertures addressed simultaneously. Referring to Table 3 (right-hand column) and to FIG. 6(b), it can be seen that the difference ($\Delta$P82, $\Delta$P84) of battery power (Pbat) required for generating an optical power (Popt=Popt1 or Popt2<Popt4) by a conventional LED or VCSEL (corresponding to addressing the equivalent of M=8 apertures of a corresponding non-addressable array of M=8 VCSEL's) and by an array of M=8 VCSEL addressing m=2 or 4 apertures, respectively, is four times or twice the value of the threshold power (Pth2) required for activating m=2 VCSEL apertures (53a).

Optimization of Both Light Source (53) and PV-Unit (61) in Combination

In a third aspect of the present invention, the energy transfer chain can be optimized in situ at the level of both light source (53) and PV-unit (61) in combination to reduce the battery power (Pbat) consumption required for generating electric pulses of target intensity (It) between the electrodes (65). The opto-AIMD of the third aspect of the present invention combines a PV-unit (61) allowing optimization of the configuration of the N PV-cells as discussed supra and a light source (53) comprising an individually addressable array of optical emitters (53a), preferably of VCSEL's. This embodiment is advantageous because once the regulation unit has determined the optimal value of Us requiring an optimal optical power value (Popt=Popt1, Popt2, or Popt4) for generating the target intensity (It), the regulation unit then determines an optimal number (m≤M) of apertures addressed at a time such as to minimize the battery power (Pbat) required to generate the optimal optical power (Popt=Popt1, Popt2, or Popt4). The combination of the in-situ optimization of the configuration of the energy transfer chain at the level of both light source (53) and PV-unit (61) in combination allows saving substantial battery power (Pbat) consumption compared with state-of-the-art opto-AIMD's (combine Tables 2 and 3).

Regulation Unit

The regulation unit has been described supra for at least determining the optimal value of Us for a given patient, and for instructing the switch control module for controlling the switches (S1-S6) of the electrical circuit to reach a PV-unit configuration characterized by the optimal value of Us. The regulation unit either, can be fully integrated in the implanted controller (54) or can comprise a coupling portion belonging to the electrical circuit (62) of the tissue coupling unit (60), and an encapsulated portion belonging to the implanted controller (54).

In the embodiment wherein the regulation unit can be fully integrated in the implanted controller (54), the regulation unit is configured for determining,
- the values of the voltage (u) and/or the intensity (I) of the electrical pulses delivered to the electrodes measured by a sensing unit,
- the required power of the optical energy pulse for reaching the target intensity (It), and/or
- the optimal optical power (Popt) required for delivering a current of the target intensity to the electrodes (65).

In the embodiment wherein the regulation unit comprises a coupling portion and an encapsulated portion, the coupling portion can be configured for determining,
- the values of the voltage (u) and/or the intensity (I) of the electrical pulses delivered to the electrodes measured by a sensing unit,
- the optimal value of Us (or Up) and the optimal optical power (Popt) of the optical energy pulse for reaching the target intensity (It).

The encapsulated portion can be configured for determining the optimal number (m) of apertures in an AIMD provided with an array of addressable optical emitters, for generating the optical energy pulse of the optical power (Popt) required for generating a current of the target intensity (It).

Communication Unit

As discussed supra, the regulation unit may comprise a coupling portion lodged in the tissue coupling unit (60) and an encapsulation portion lodged in the encapsulation unit. The coupling and encapsulation portions of the regulation unit must be able to communicate with one another. Furthermore, optimization of the PV-unit (61) as well as of the light source (53) require information exchanges between the encapsulation unit (50) and the tissue coupling unit (60), since the optical power (Popt) generated by the light source (53) in the encapsulation unit (50) depends on the configuration (Us) of the PV-unit in the tissue coupling unit (60). It is therefore preferred that the opto-AIMD comprises a communication unit for sending data between the encapsulation unit and the tissue coupling unit, as illustrated in FIGS. 8(a) to 8(c).

The communication unit may be configured for sending data one way from the encapsulation unit (50) to the tissue coupling unit (60) or reverse. Alternatively, the communication unit may be configured for sending data two ways from and to the encapsulation unit (50) to and from the tissue coupling unit (60).

The communication unit comprises,
- a photodetector (63p) and/or a communication light source (63Lc), preferably a LED or a laser (e.g., VCSEL), coupled to the electrical circuit (62) of the tissue coupling unit,
- a photodetector (53p) and/or communication light source (53Lc), preferably a LED, coupled to the implanted controller (54) enclosed in the encapsulation unit, and
- one or two communication optical fibres (41c, 41c1, 41c2).

Figure 8A:
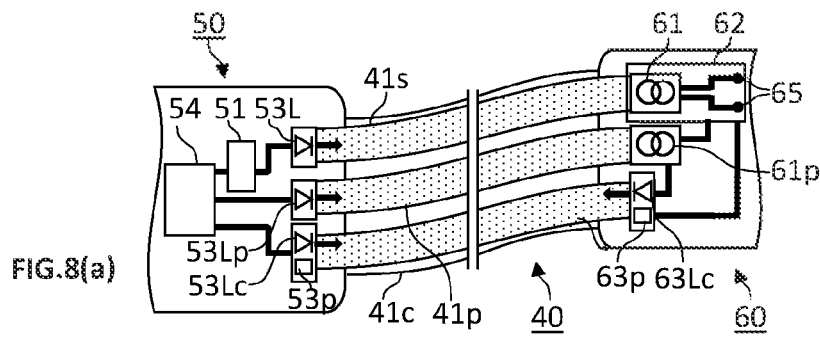
FIGS. 8(a) to 8(c): show various embodiments of energy transfer chains between the encapsulation unit and the tissue coupling unit.
Figure 8B:
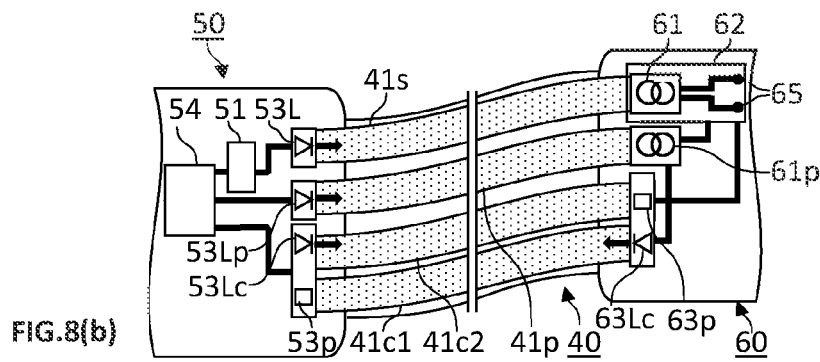
Figure 8C:
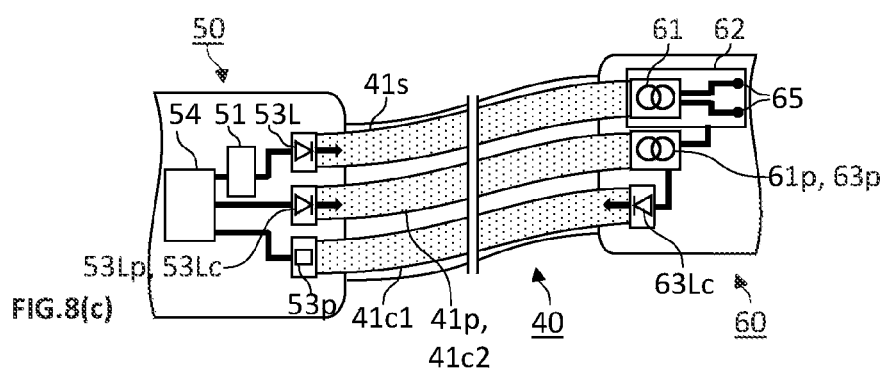

In one embodiment illustrated in FIG. 8(a), a single communication optical fibre (41c) is used, which is different from the stimulation optical fibre (41s) and preferably comprised in the implanted energy transfer unit (40). The single communication optical fibre (41c) comprises a proximal end coupled to the encapsulation unit in optical communication with the photodetector (53p) and/or with the communication light source (53Lc) enclosed in the encapsulation unit (50), and a distal end coupled to the tissue coupling unit (60) in optical communication with the communication light source (63Lc) and/or with the photodetector (63p) of the tissue coupling unit, respectively. As shown in FIG. 8(a), for two-way communication using a single communication optical fibre (41c), a communication light source (53Lc) and a photodetector (53p) lodged in the encapsulation unit (50) face the proximal end of the single communication optical fibre (41c). Similarly, a communication light source (63Lc) and a photodetector (63p) lodged in the tissue coupling unit (60) face the distal end of the single communication optical fibre (41c). The communication light sources (53Lc, 63Lc) lodged in the encapsulation unit and in the tissue coupling unit, emit an optical signal comprising data. The photodetectors (53p, 63p) lodged in the tissue coupling unit and in the encapsulation unit each receive the optical signal and transform it into an electrical signal transferred to a processing unit, which can be formed by or part of the implanted controller (54), or the regulation unit, or the electrical circuit, or the switch control module. The photodetectors (53p, 63p) can be any type of photodetector known in the art, including a photovoltaic cell.

In an alternative embodiment illustrated in FIGS. 8(b) and 8(c), two communication optical fibres are used, comprising first and second communication optical fibres (41c1, 41c2). The first communication optical fibre (41c1) is different from the stimulation optical fibre (41s) and is preferably comprised in the implanted energy transfer unit (40). The first communication optical fibre (41c1) comprises a proximal end coupled to the encapsulation unit in optical communication with the photodetector (53p) enclosed in the encapsulation unit, and a distal end coupled to the tissue coupling unit in optical communication with the communication light source (63Lc) of the tissue coupling unit.

The second communication optical fibre (41c2) is different from both stimulation optical fibre (41s) and first communication optical fibre (41c1), and is preferably comprised in the implanted energy transfer unit (40). The second communication optical fibre (41c2) comprises a proximal end coupled to the encapsulation unit in optical communication with the communication light source (53Lc) enclosed in the encapsulation unit, and a distal end coupled to the tissue coupling unit in optical communication with the photodetector (63p) of the tissue coupling unit.

As shown in FIGS. 8(b) and 8(c), a communication light source (53Lc) lodged in the encapsulation unit (50) faces the proximal end of the second communication optical fibre (41c2) and a photodetector (53p) also lodged in the encapsulation unit (50) faces the proximal end of the first communication optical fibre (41c1). Similarly, a communication light source (63Lc) lodged in the tissue coupling unit (60) faces the distal end of the first communication optical fibre (41c1) and a photodetector (63p) also lodged in the tissue coupling unit (60) faces the distal end of the second communication optical fibre (41c2).

The choice of a communication unit comprising a single or two distinct communication optical fibres (41c, 41c1, 41c2) depends on a number of parameters. A communication unit comprising a single communication optical fibre (41c) is more compact, but data can be transferred in one direction between the encapsulation unit (50) and the tissue coupling unit (60) only sequentially with the transfer of data in the other direction. A communication unit comprising two distinct communication optical fibres (41c1, 41c2) allows simultaneous transfer of data in both directions between the encapsulation unit (50) and the tissue coupling unit (60) but is bulkier and more expensive as two optical fibres must be coupled to the encapsulation unit (50) and to the tissue coupling unit (60).

The data sent via the communication unit from the encapsulation unit to the tissue coupling unit can comprise one or more of,
- the value of the target intensity (It) to be generated between the electrodes (65),
- the values of Us (or Up) of the PV-unit before sending a pulse, in case the regulation unit is lodged, at least partly, in the encapsulation unit, and/or the status of the switches required for reaching the corresponding values of Us (or Up),
- in case the tissue coupling unit comprises more than two electrodes, the specific pair of electrodes wherein the current of target intensity is to be directed.

The data sent via the communication unit from the tissue coupling unit to the encapsulation unit can include one or more of,
- confirmation that the switches are configured according to the values of Us (or Up) received from the encapsulation unit,
- confirmation that an electrical pulse was delivered to the electrodes (65),
- the values of the voltage (u) and/or the intensity (I) of the electrical pulses delivered to the electrodes measured by a sensing unit,
- a value of the required optical power (Popt) of the optical energy pulse for generating the target intensity (It), in embodiments wherein the regulation unit is at least partly lodged in the tissue coupling unit (60).

Power Transfer Unit

The tissue coupling unit (60) can require power. For example, power may be required to actuate the regulation unit, in case it is at least partly lodged in the tissue coupling unit, and for actuating the switches (S1-S6) of the PV-unit (61) to change the configuration thereof according to the value of Us. Also, power may be needed to energize a communication light source (63Lc) lodged in the tissue coupling unit. The energy transfer chain for generating electrical pulses comprising the light source (53L), the stimulation optical fibre (41s) and the PV-unit (61) could be used to energize the elements of the electrical circuit. This solution has a drawback that it can be complex to send to the tissue coupling unit (60) in a controlled manner stimulation pulses of the required optical power (Popt) and, at the same time, optical power for energizing the components of the tissue coupling unit.

In a preferred embodiment, the opto-AIMD comprises a power transfer unit for transferring power from the encapsulation unit (50) to the tissue coupling unit (60). As illustrated in FIGS. 8(a) to 8(c), the power transfer unit comprises,
- one or more power photovoltaic cells (61p) coupled to the electrical circuit (62) of the tissue coupling unit,
- a power light source (53Lp), preferably a LED or laser (e.g., VCSEL), coupled to the implanted controller (54) enclosed in the encapsulation unit, and
- a power optical fibre (41c) different from the stimulation optical fibre (41s) and preferably different from the one or two communication optical fibres (41c), and preferably comprised in the implanted energy transfer unit (40).

The power optical fibre (41p) comprises a proximal end coupled to the encapsulation unit in optical communication with the power light source (53Lp) enclosed in the encapsulation unit, and a distal end coupled to the tissue coupling unit in optical communication with the one or more power photovoltaic cells (61p) of the tissue coupling unit; for energizing the electrical circuit (62).

In an embodiment illustrated in FIGS. 8(a) and 8(b), the power transfer unit comprises its own power optical fibre (41p), distinct from the stimulation optical fibre (41s) and from the single or first and second communication fibres (41c, 41c1, 41c2).

Alternatively, the power transfer unit can share the power optical fibre (41p) with a communication optical fibre (41c, 41c1, 41c2) or with the stimulation optical fibre (41s). It was discussed supra that sharing the power optical fibre (41p) with the stimulation optical fibres (41s) could be complex as it may become difficult to control with sufficient accuracy the intensity of the current thus generated. As illustrated in FIG. 8(c), however, sharing the power optical fibre (41p) with a communication optical fibre (41c, 41c1, 41c2), preferably with the second communication optical fibre (41c2) is quite convenient, as it is easy to send simultaneously through the common power/communication optical fibre (41p, 41c2) a first optical component for energizing elements of the tissue coupling unit (60) and a second component, e.g., in frequency modulation, for sending data to the tissue coupling unit. In this embodiment, the communication light source (43Lc) can be the same as or different from the power light source (53Lp).

CONCLUDING REMARKS

The opto-AIMD of the present invention is the first to our knowledge allowing optimizing the energy transfer chain extending from the light source (53L) to the electrodes (65) in situ after implantation of the AIMD in a patient. In situ optimization of either or both the PV-unit (61) and the/or the light source (53L) using an array of addressable light emitters (53a) can save substantial amounts of battery power (Pbat). The service life of a battery (54) or the period between two charging operations of a rechargeable battery or a supercapacitor, can be increased substantially to the full benefits and comfort of the patients.

Optimizing either the PV-unit (61) or the light source (63) as described supra already yields substantial saving in battery power. But combining optimization of both PV-unit and light source is particularly advantageous in terms of power management and savings. One major challenge with opto-AIMD's of reducing energy losses along the energy transfer chain is solved with the present invention. The gist of the present invention is to be able to optimize the energy transfer chain in situ after the opto-AIMD was implanted in a patient. This is essential, since the value of the impedance (2) measured between the electrodes (65) is critical for determining the optical power (Popt) required for generating a current of target intensity (It). Yet, the impedance (Z) is impossible to assess without measuring directly in the patient.

Addressing individually the apertures of an optical emitters array also allows substantial savings of battery power (Pbat) when, at the same time, allowing a wide range of optical powers (Popt) to be delivered depending on the desired value of the target intensity (It).

The present invention is particularly advantageous when a recovery pulse follows a stimulation pulse for neutralizing any deposition of charges in the tissues. The stimulation and recovery pulses are related by the product, It×ts=Ir×tr, wherein It is the target intensity of a stimulation pulse, Ir the recovery intensity, and ts and tr are the durations of the stimulation and recovery pulses, respectively, with It>Ir. It has been seen supra that varying the intensity of current to be generated between the electrodes (65) with a state-of-the-art AIMD can lead to substantial battery power (Pbat) waste, as at least one of, generally both PV-unit and light source are working in sub-optimal conditions. With the AIMD of the present invention, any one of or both PV-unit (61) and light source (53L) can be optimized in situ, to match different values of target and recovery intensities (It, Ir) to be generated sequentially one after the other.

| REF | DESCRIPTION |
| --- | --- |
| 40 | Energy transfer unit |
| 41c | Single communication optical fibre |
| 41c1, 41c2 | First and second communication optical fibre |
| 41p | Power optical fibre |
| 41s | Stimulation optical fibre |
| 50 | Encapsulation unit |
| 51 | Implanted pulse generator (IPG) |
| 52 | Source of power |
| 53a | VCSEL aperture |
| 53e | VCSEL electrical contacts |
| 53L | Light source |
| 53Lc | Communication light source at encapsulation unit |
| 53Lp | Power light source |
| 53p | Photodetector at encapsulation unit |
| 54 | Implanted controller |
| 55 | Source of power ((rechargeable) battery) |
| 60 | Tissue coupling unit |
| 61 | Photovoltaic unit |
| 61p | Photovoltaic cell |
| 61p1-61p4 | PV-cells in PV-unit comprising N = 4 PV-cells |
| 61i | $i^{th}$ photovoltaic cell |
| 62 | Electrical circuit |
| 63p | Photodetector at tissue coupling unit |
| 63Lc | Communication light source at tissue coupling unit |
| 64 | Insulated support |
| 65 | Electrode |
| I | Intensity |
| I0 | Estimated intensity |
| Im | Maximum intensity of a PV-unit configuration |
| It | Target intensity |
| M | Number of VSEL apertures |
| m | number of addressed apertures |
| N | Number of photovoltaic cells (61p) |
| Pbat | Power provided by the source of power ((rechargeable) battery) |
| Popt1, 2, 4 | Optical power values required for I = It, N = 4, and Us = 1, 2, 4 |
| Pb1, 2, 4 | Optimal battery power required for yielding Popt1, Popt2, Popt4 |
| Pe | Maximum efficiency of a PV-cell unit |
| Pei | Efficiency at Z = i |
| Popt | Optical power |
| PoptINV | Optical power with AIMD according to the resent invention |
| PoptPA | Optical power with state-of-the-art AIMD |
| Pp | Number of PV-cells in parallel in each of the Us units |
| Ps | Number of PV-cells in series in each of the Up units |
| S1-S6 | switches |
| u | Voltage |
| u0 | Estimated voltage |
| uei | Maximum efficiency voltage of PV configuration Us = i |
| um | Maximum voltage of a PV-unit configuration |
| umi | Maximum voltage of PV-unit configuration Us = i |
| Up | Number of units in parallel |
| Us | Number of units in series |
| ut | Target voltage |
| Z | impedance |
| Z0 | Estilated impedance |
| Z1-Z3 | Examples of impedance values |

The invention claimed is:

1. An active implantable medical device (AIMD), for electrical stimulation of a tissue, the AIMD comprising:

an encapsulation unit (50) suitable for being subcutaneously implanted and comprising a housing (50h) enclosing,
- an implanted energy pulse generator (IPG) (51) coupled to a light source (53L), for delivering optical energy pulses of optical power (Popt),
- a source of power (52) for activating the IPG (51) and configured for generating a battery power (Pbat) which can be varied,
- an implanted controller (54) configured for instructing the IPG to deliver optical energy pulses of a given optical power (Popt) as a function of time, and
- an implanted energy transfer unit (40) comprising a stimulation optical fibre (41s) comprising a proximal end optically coupled to the light source, and a distal end coupled to a tissue coupling unit (60), for transferring optical energy from the light source of the encapsulation unit to the tissue coupling unit (60),
- the tissue coupling unit (60) suitable for being subcutaneously implanted and coupled to a tissue at a location separated from the encapsulation unit (50), and comprising,
  - an insulating support (64) supporting,
  - an electrical circuit (62) configured for delivering electrical pulses of a given target intensity (It) and comprising,
    - a photovoltaic unit (PV-unit) (61) comprising N≥2 photovoltaic (PV) cells (61p), positioned in optical contact with the distal end of the optical fibre (41s) for transforming the optical energy pulses transmitted by the optical fibre into electrical energy pulses of the target intensity (It),
    - electrical conductors for transferring the electrical energy pulses to electrodes (61) mounted on the insulation support (64) such as to be in electrical contact with the tissue when the insulation support is coupled to the tissue, wherein
- the PV-unit comprises Us units arranged in series, each unit comprising Pp photovoltaic cells (PV-cells) arranged in parallel, or Up units arranged in parallel, each unit comprising Ps PV-cells arranged in series, wherein Us, Up, Pp, and Ps∈N, and Us×Pp=Up×Ps=N=constant,
- the electrical circuit (62) comprises switches configured for varying the values of Us and Up, and wherein
- the electrical circuit (62) comprises a switch control module configured for controlling the switches yielding optimized values of Us or Up, such that the power (Popt) of the optical energy pulses required for yielding the electrical pulses of the given target intensity (It) is minimized.

2. The AIMD according to claim 1, further comprising a regulation unit configured for determining the optimized values of Us or Up, wherein the electrical circuit (62) comprises a sensing unit configured for measuring values of at least one of a voltage (u) or an intensity (I) of the electrical pulses delivered to the electrodes, and wherein measured values of at least one of the voltage (u) or the intensity (I) are used by the regulation unit for optimizing the values of Us or Up.

3. The AIMD according to claim 2, wherein the regulation unit is configured for determining the optimized values of Us or Up, as follows,
- for a given value of the optical power (Popt), determining or measuring a target voltage (ut) corresponding to the target intensity (It) when the AIMD is implanted with the tissue coupling unit (60) coupled to a tissue,
- determining an optimal value of Us or Up yielding a maximum voltage (um1, um2, um4) which is larger than, and the closest to the value of the target voltage (ut), and
- adjusting the power (Popt) of the optical energy pulses to an optimal optical power (Popt1, Popt2, Popt4) required to reach the target intensity (It) with the optimal value of Us or Up.

4. The AIMD according to claim 3, wherein the regulation unit is configured for determining or measuring the target voltage (ut) as follows, either
- generating and transmitting optical pulses of a given optical power (Popt) known to yield upon irradiation of the PV-unit with Us=N (or Up=1), a current of the target intensity (It), and measuring a voltage between the electrodes (61) which corresponds to the target voltage (ut), or
- for any given value of the optical power (Popt) and with Us=N (or Up=1),
  - measuring a voltage (u) and an intensity (I) between the electrodes (61),
  - determining an impedance (Z) with |Z|=|u|/|I|, and
  - calculating the target voltage (ut) with |ut|=|Z|×|It|.

5. The AIMD according to claim 3, wherein once the regulation unit has determined the optimal value of Us requiring an optimal optical power value (Popt=Popt1, Popt2, or Popt4) for generating the target intensity (It), the regulation unit is configured for then determining an optimal number (m≤M) of apertures addressed at a time such as to minimize the battery power (Pbat) required to generate the optimal optical power (Popt=Popt1, Popt2, or Popt4).

6. The AIMD according to claim 3, wherein the PV unit contains Nt PV-cells and wherein the regulation unit is configured for determining the optimized values of Us or Up with different values of N≤Nt.

7. The AIMD according to claim 2, wherein a communication unit for sending data between the encapsulation unit and the tissue coupling unit, wherein the communication unit comprises,
- at least one of a photodetector (63p) or a communication light source (63Lc) coupled to the electrical circuit (62) of the tissue coupling unit,
- at least one of a photodetector (53p) or a communication light source (53Lc) coupled to the implanted controller (54) enclosed in the encapsulation unit, and
- one or two communication optical fibres arranged as follows, either
  - a single communication optical fibre (41c) different from the stimulation optical fibre (41s) and preferably comprised in the implanted energy transfer unit (40), the single communication optical fibre comprising a proximal end coupled to the encapsulation unit in optical communication with at least one of the photodetector (53p) or with the communication light source (53Lc) enclosed in the encapsulation unit, and a distal end coupled to the tissue coupling unit in optical communication with at least one of the communication light source (63Lc) or with the photodetector (63p) of the tissue coupling unit, respectively, or two communication optical fibres, comprising
    - a first communication optical fibre different from the stimulation optical fibre (41s) and preferably comprised in the implanted energy transfer unit (40), comprising a proximal end coupled to the encapsulation unit in optical communication with the photodetector (53*p*) enclosed in the encapsulation unit, and a distal end coupled to the tissue coupling unit in optical communication with the communication light source (63Lc) of the tissue coupling unit, and a second communication optical fibre different from both stimulation optical fibre (41*s*) and first communication optical fibre, and located in the implanted energy transfer unit (40), comprising a proximal end coupled to the encapsulation unit in optical communication with the communication light source (53Lc) enclosed in the encapsulation unit, and a distal end coupled to the tissue coupling unit in optical communication with the photodetector (63*p*) of the tissue coupling unit wherein the regulation unit either, is fully integrated in the implanted controller (54) and is configured for determining,
the values of at least one of the voltage (u) or
the intensity (I) of the electrical pulses delivered to the electrodes measured by the sensing unit, the optimal values of Us and Pp for reaching the target intensity (It), and
wherein the regulation unit is configured for determining the optimized values of Us or Up, as follows,
for a given value of the optical power (Popt), determining or measuring a target voltage (ut) corresponding to the target intensity (It) when the AIMD is implanted with the tissue coupling unit (60) coupled to a tissue,
determining an optimal value of Us or Up yielding a maximum voltage (um1, um2, um4) which is larger than, and the closest to the value of the target voltage (ut),
adjusting the power (Popt) of the optical energy pulses to an optimal optical power (Popt1, Popt2, Popt4) required to reach the target intensity (It) with the optimal value of Us or Up,
the optimal optical power (Popt), comprises a coupling portion belonging to the electrical circuit (62) of the tissue coupling unit (60) and is configured for determining,
the values of the voltage (u) and/or the intensity (I) of the electrical pulses delivered to the electrodes measured by the sensing unit,
the optimal value of Us or Up and the optimal optical power (Popt) of the optical energy pulse for reaching the target intensity (It), and
comprises an encapsulated portion belonging to the implanted controller (54) in the encapsulation unit (50) and is configured for determining,
the optimal number (m) of apertures that are addressed at a time such as to minimize the battery power (Pbat) to generate the optimal optical power (Popt) for generating the optical energy pulse of the optimal optical power (Popt).

8. The AIMD according to claim 7, further comprising a power transfer unit for transferring power from the encapsulation unit (50) to the tissue coupling unit (60), the power transfer unit comprising, one or more power photovoltaic cells (61*p*) coupled to the electrical circuit (62) of the tissue coupling unit, a power light source (53Lp), coupled to the implanted controller (54) enclosed in the encapsulation unit, and a power optical fibre (41*p*) different from the stimulation optical fibre (41*s*) and different from the one or two communication optical fibres (41*c*, 41*c*1, 41*c*2), the power optical fibre (41*p*) comprising a proximal end coupled to the encapsulation unit in optical communication with the power light source (53Lp) enclosed in the encapsulation unit, and a distal end coupled to the tissue coupling unit in optical communication with the one or more power photovoltaic cells (61*p*) of the tissue coupling unit, for energizing the electrical circuit (62).

9. The AIMD according to claim 8, wherein the communication light source (53Lc) is the same as the power light source (56L), and wherein the power optical fibre (41*p*) is the same as the single communication optical fibre (41*c*) or is the same as the second communication optical fibre.

10. The AIMD according to claim 7, wherein the data sent via the communication unit between the encapsulation unit and the tissue coupling unit comprises one or more of, from the tissue coupling unit to the encapsulation unit, including one or more of,
confirmation that an electrical pulse was delivered to the electrodes,
at least one of the values of the voltage (u) or the intensity (I) of the electrical pulses delivered to the electrodes measured by the sensing unit configured for measuring values of at least one of a voltage (u) or an intensity (I) of the electrical pulses delivered to the electrodes, and wherein measured values of at least one of the voltage (u) or intensity (I) are used by the regulation unit for optimizing the values of Us or U,
a value of the required optical power (Popt1, Popt2, Popt4) of the optical energy pulse for generating the target intensity (It),
from the encapsulation unit to the tissue coupling unit, including one or more of,
the value of the target intensity (It), or
the optimized values of Us or Up.

11. The AIMD according to claim 2, wherein the PV unit contains Nt PV-cells and wherein the regulation unit is configured for determining the optimized values of Us or Up with different values of N≤Nt.

12. The AIMD according to claim 2, wherein the regulation unit is configured for determining or measuring the target voltage (ut) as follows, either generating and transmitting optical pulses of a given optical power (Popt) known to yield upon irradiation of the PV-unit with Us=N (or Up=1), a current of the target intensity (It), and measuring a voltage between the electrodes (61) which corresponds to the target voltage (ut), or
for any given value of the optical power (Popt) and with Us=N (or Up=1),
measuring a voltage (u) and an intensity (I) between the electrodes (61),
determining an impedance (Z) with |Z|=|u|/|I|, and
calculating the target voltage (ut) with |ut|=|Z|×|It|.

13. The AIMD according to claim 1, wherein the light source (51L) is an addressable optical emitters array, the optical emitters array comprising M>1 apertures addressable independently one by one or by sub-groups of apertures.

14. The AIMD according to claim 13, wherein the addressable optical emitters array is an array of addressable laser emitter diodes, a vertical cavity surface-emitting laser (VCSEL), or an array of addressable light emitting diodes (LED).

15. The AIMD according to claim 1, comprising a communication unit for sending data between the encapsulation unit and the tissue coupling unit, wherein the communication unit comprises, at least one of a photodetector (63*p*) or a communication light source (63Lc) coupled to the electrical circuit (62) of the tissue coupling unit, at least one of a photodetector (53p) or a communication light source (53Lc) coupled to the implanted controller (54) enclosed in the encapsulation unit, and one or two communication optical fibres arranged as follows, either a single communication optical fibre (41c) different from the stimulation optical fibre (41s) and located in the implanted energy transfer unit (40), the single communication optical fibre comprising a proximal end coupled to the encapsulation unit in optical communication with at least one of the photodetector (53p) or with the communication light source (53Lc) enclosed in the encapsulation unit, and a distal end coupled to the tissue coupling unit in optical communication with at least one of the communication light source (63Lc) or with the photodetector (63p) of the tissue coupling unit, respectively, or two communication optical fibres, comprising a first communication optical fibre different from the stimulation optical fibre (41s) and located in the implanted energy transfer unit (40), comprising a proximal end coupled to the encapsulation unit in optical communication with the photodetector (53p) enclosed in the encapsulation unit, and a distal end coupled to the tissue coupling unit in optical communication with the communication light source (63Lc) of the tissue coupling unit, and a second communication optical fibre different from both the stimulation optical fibre (41s) and the first communication optical fibre, comprising a proximal end coupled to the encapsulation unit in optical communication with the communication light source (53Lc) enclosed in the encapsulation unit, and a distal end coupled to the tissue coupling unit in optical communication with the photodetector (63p) of the tissue coupling unit.

16. The AIMD according to claim 15, wherein the data sent via the communication unit between the encapsulation unit and the tissue coupling unit comprises one or more of, from the tissue coupling unit to the encapsulation unit, including one or more of, confirmation that an electrical pulse was delivered to the electrodes, at least one of the values of the voltage (u) or the intensity (I) of the electrical pulses delivered to the electrodes measured by the sensing unit configured for measuring values of at least one of a voltage (u) or an intensity (I) of the electrical pulses delivered to the electrodes, and wherein measured values of at least one of the voltage (u) or intensity (I) are used by the regulation unit for optimizing the values of Us or Up, a value of the required optical power (Popt1, Popt2, Popt4) of the optical energy pulse for generating the target intensity (It), from the encapsulation unit to the tissue coupling unit, including one or more of, the value of the target intensity (It), or the optimized values of Us or Up.

17. The AIMD according to claim 15, wherein the communication light source (53Lc) is a LED.

18. An active implantable medical device (AIMD), for electrical stimulation of a tissue, the AIMD comprising:

an encapsulation unit (50) suitable for being subcutaneously implanted and comprising a housing (50h) enclosing, an implanted energy pulse generator (IPG) (51) coupled to a light source (53L), for delivering optical energy pulses of optical power (Popt), a source of power (52) for activating the IPG (51) and configured for generating a battery power (Pbat) which can be varied, an implanted controller (54) configured for instructing the IPG to deliver optical energy pulses of a given power (Popt) as a function of time, and an implanted energy transfer unit (40) comprising a stimulation optical fibre (41s) comprising a proximal end optically coupled to the light source (53L), and a distal end coupled to a tissue coupling unit (60), for transferring optical energy from the light source (53L) of the encapsulation unit to the tissue coupling unit (60), the tissue coupling unit (60) is suitable for being subcutaneously implanted and coupled to a tissue at a location separated from the encapsulation unit (60) and comprises, an insulating support (64) supporting, an electrical circuit (62) configured for delivering electrical pulses of a given target intensity (It) and comprising, a photovoltaic unit (PV-unit) (61) comprising one or more photovoltaic (PV) cells (61p), positioned in optical contact with the distal end of the optical fibre (41s) for transforming the optical energy pulses transmitted by the optical fibre into electrical energy pulses of the target intensity (It), electrical conductors for transferring the electrical energy pulses to electrodes (61) mounted on the insulation support (64) such as to be in electrical contact with the tissue when the insulation support is coupled to the tissue, wherein the light source (53L) is an addressable optical emitters array, the optical emitters array comprising M>1 apertures addressable independently one by one or by sub-groups of apertures, and wherein the implanted controller (54) is configured for determining an optimal number (m≤M) of apertures addressed at a time such as to minimize the battery power (Pbat) to generate the optimal optical power (Popt).

* * * * *